US012622572B2

(12) United States Patent
Shiota et al.

(10) Patent No.: US 12,622,572 B2
(45) Date of Patent: May 12, 2026

(54) ENDOSCOPIC TREATMENT TOOL

(71) Applicant: OLYMPUS MEDICAL SYSTEMS CORP., Tokyo (JP)

(72) Inventors: Yusuke Shiota, Machida (JP); Kotaro Yamada, Tachikawa (JP); Daiki Hagiwara, Hachioji (JP); Hiromasa Kato, Tokyo (JP); Chika Miyajima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 610 days.

(21) Appl. No.: 18/104,879

(22) Filed: Feb. 2, 2023

(65) Prior Publication Data

US 2023/0240514 A1     Aug. 3, 2023

Related U.S. Application Data

(60) Provisional application No. 63/306,154, filed on Feb. 3, 2022.

(51) Int. Cl.
*A61B 1/00* (2006.01)

(52) U.S. Cl.
CPC ...... *A61B 1/00087* (2013.01); *A61B 1/00042* (2022.02); *A61B 1/00066* (2013.01); *A61B 1/00124* (2013.01)

(58) Field of Classification Search
CPC ............ A61B 1/00087; A61B 1/00042; A61B 1/00066; A61B 1/00124
USPC .................................... 606/32; 600/104, 106
See application file for complete search history.

(56) References Cited

U.S. PATENT DOCUMENTS

| | | | | |
|---|---|---|---|---|
| 2008/0269558 A1* | 10/2008 | Yahagi | ............... | A61B 18/1477 600/106 |
| 2009/0036737 A1* | 2/2009 | Muyari | .............. | A61B 18/1492 600/106 |
| 2009/0112225 A1* | 4/2009 | Kaneko | ............ | A61B 17/32056 606/113 |
| 2022/0241022 A1* | 8/2022 | Cohen | .................... | A61B 90/39 |
| 2022/0313356 A1* | 10/2022 | Higuchi | ............. | A61B 18/1492 |
| 2023/0136593 A1* | 5/2023 | Yamada | ........... | A61B 17/00234 600/106 |

FOREIGN PATENT DOCUMENTS

| | | | |
|---|---|---|---|
| JP | 2009-034388 A | 2/2009 | |
| WO | WO-2015133429 A1 * | 9/2015 | ......... A61B 1/00087 |

* cited by examiner

*Primary Examiner* — Beverly M Flanagan
(74) *Attorney, Agent, or Firm* — Morgan, Lewis & Bockius LLP

(57) ABSTRACT

An endoscope treatment tool, comprising: a sheath; a handle body; a wire; a treatment portion connected to a distal end of the wire and arranged on a distal end side of the sheath; a rotating handle movable with respect to the handle body and connected to the wire; a conductive connector having an insertion passage through which the wire is inserted, wherein the wire is movable in a wire movement direction to advance and retreat in a direction that is parallel to a longitudinal axis of the handle body, wherein the wire is rotatable around an axis of the wire movement direction, and wherein the conductive connector extends in a direction that intersects the wire movement direction.

20 Claims, 27 Drawing Sheets

ENDOSCOPIC TREATMENT TOOL

CROSS-REFERENCE TO RELATED APPLICATIONS

The present application claims priority based on U.S. Patent Provisional Application No. 63/306,154 filed in the United States on Feb. 3, 2022, the entire contents of which are incorporated herein by reference.

BACKGROUND

Technical Field

The present invention relates to an endoscopic treatment tool.

Background Art

Conventionally, in endoscopic treatment, endoscopic treatment tools equipped with high-frequency treatment devices such as hemostatic forceps and high-frequency knives that apply high-frequency current to cauterize a bleeding target to stop bleeding have been used. A high-frequency current is supplied to a wire connected to a high-frequency treatment device via an A cord (active cord) connected to a connector provided in an operation portion of an endoscope treatment tool.

When the high-frequency treatment device needs to be rotated, the wire connected to the high-frequency treatment device is attached to the operation portion so as to be rotatable around the longitudinal axis of the operation portion. In this case, when the wire is rotated to rotate the high-frequency treatment device, the connector attached to the wire also rotates, so the A cord is likely to wind around the operation portion.

The endoscopic treatment tool described in Japanese Unexamined Patent Application, First Publication No. 2009-034388 (hereinafter referred to as Patent Document 1) can rotate only the wire without rotating the connector around the longitudinal axis by rotating the handle, thereby rotating the distal end mechanism. The energizing plug is attached to a non-rotating operating member and does not rotate even when the tip mechanism is rotated.

However, in the endoscopic treatment tool described in Patent Document 1, the energizing plug and the wire are connected by an elastic conducting portion. An elastic conductor may interfere with the movement of the wire, for example. Therefore, in the endoscopic treatment tool described in Patent Document 1, the connection mode between the energizing plug and the wire was not always optimal.

SUMMARY

In view of the above circumstances, it is an object of the present invention to provide an endoscopic treatment tool in which a connector to which a high-frequency current is supplied does not rotate and the connector and a wire connected to a high-frequency treatment device are connected.

In order to solve the above problems, the present invention proposes the following means.

A treatment tool for an endoscope according to a first aspect of the present invention includes: a sheath; a handle body attached to a proximal end of the sheath; a wire arranged so as to be capable of advancing and retreating in a direction of a longitudinal axis of the handle body and to be capable of rotating around the longitudinal axis; a treatment portion connected to a distal end of the wire and arranged on a distal end side of the sheath; a rotating handle configured to be capable of moving with respect to the handle body and connected to a proximal end of the wire; a conductive connector having an insertion passage through which the wire is inserted so as to be capable of advancing and retreating and to be capable of rotating, and extending in a direction intersecting with a direction of movement of the wire.

In the endoscopic treatment tool according to the present invention, the connector to which high-frequency current is supplied does not rotate, and the connector and the wire connected to the high-frequency treatment device are connected.

DETAILED DESCRIPTION

First Embodiment

Figure 1:
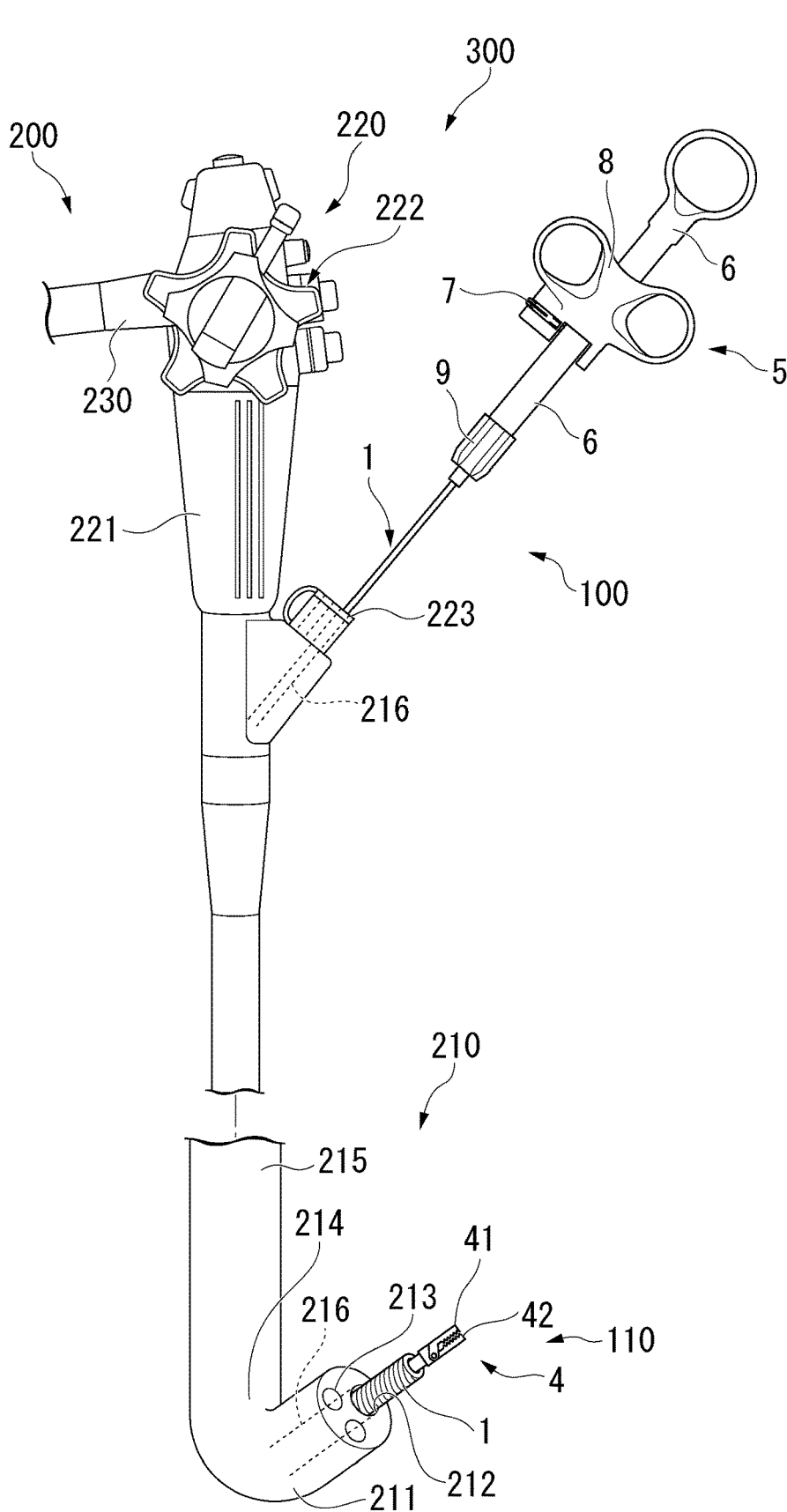
FIG. 1 is an overall view of an endoscopic treatment system provided with an endoscopic treatment tool according to a first embodiment.

An endoscope treatment system 300 including the endoscope treatment tool 100 according to the first embodiment of the present invention will be described with reference to FIGS. 1 to 13. FIG. 1 is an overall view of an endoscope treatment system 300.

[Endoscope Treatment System 300]

The endoscope treatment system 300 includes an endoscope treatment tool 100 and an endoscope 200, as shown in FIG. 1. The endoscopic treatment tool 100 is used by being inserted into an endoscope 200.

[Endoscope 200]

The endoscope 200 is a known flexible endoscope, and includes an insertion portion 210 inserted into the body from the distal end, an operation portion 220 attached to the proximal end of the insertion portion 210, and a universal cord 230 attached to the operation portion 220.

The insertion portion 210 is an elongated long member that can be inserted into the lumen. The insertion portion 210 includes a distal end portion 211, a bending portion 214, and a flexible portion 215. The distal end portion 211, the bending portion 214, and the flexible portion 215 are connected in order from the distal end side. A channel 216 for inserting the treatment tool 100 is provided inside the insertion portion 210. At the distal end portion 211, a distal opening portion 212 of a channel 216 and an imaging portion 213 are provided.

The imaging portion 213 is equipped with an imaging device such as a CCD or CMOS, for example, and is capable of imaging a region to be treated. The bending portion 214 bends according to the operation of the operation portion 220 by the user. The flexible portion 215 is a tubular portion having flexibility.

The operation portion 220 is connected to the flexible portion 215. The operation portion 220 has a grip 221, an input portion 222, and a forceps port 223. The grip 221 is a member supported by the user. The input portion 222 receives an operation input for bending the bending portion 214. The forceps port 223 is a proximal opening of the channel 216.

The universal cord 230 connects the endoscopic treatment tool 100 and an external device. The universal cord 230 is inserted with an imaging cable, an optical fiber cable, or the like for outputting an imaging signal imaged by the imaging portion 213 to the outside.

[Treatment Tool 100 for Endoscope]

Figure 2:
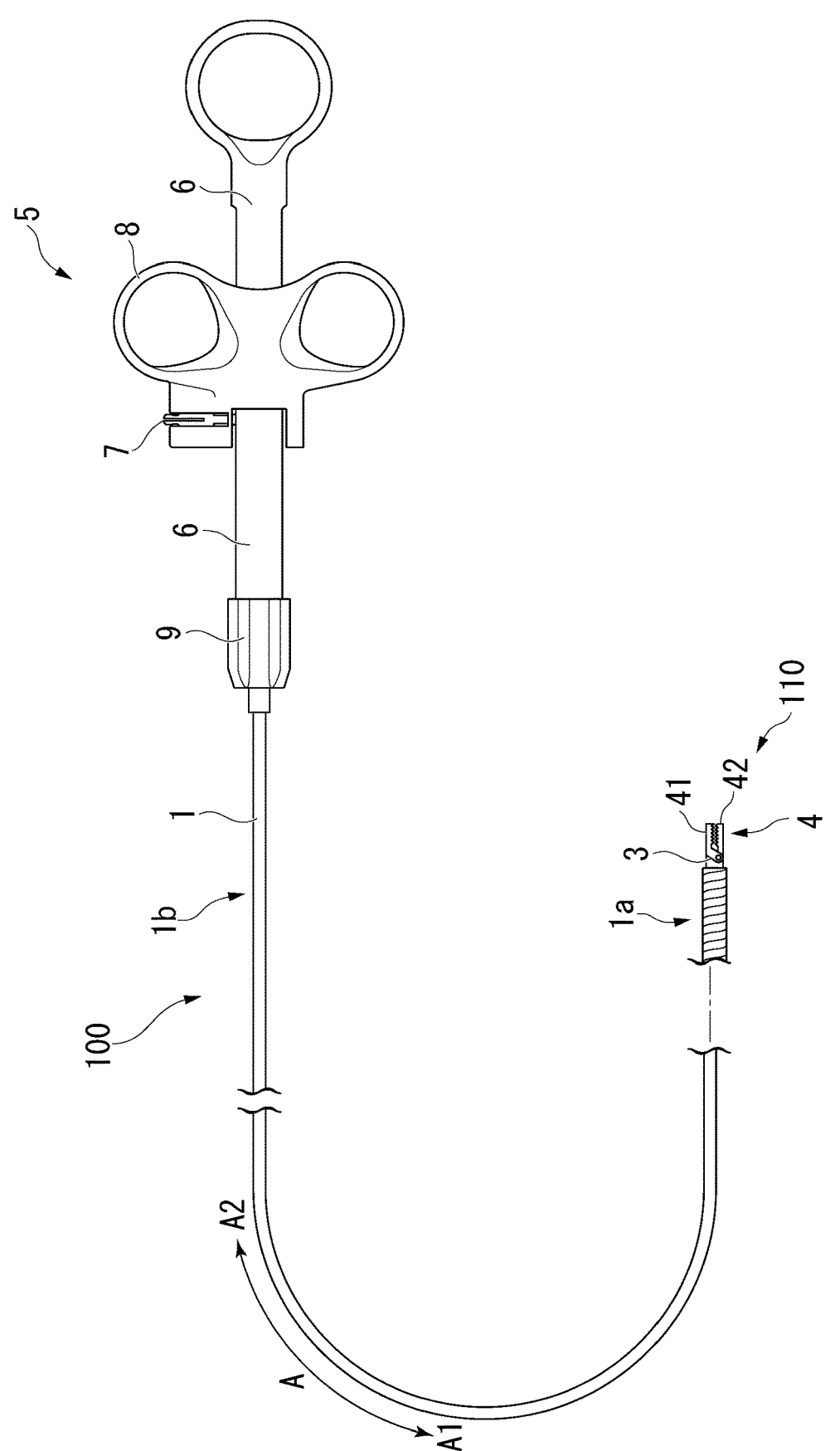
FIG. 2 is an overall view showing the endoscopic treatment tool.

FIG. 2 is an overall view showing the endoscopic treatment tool 100.

The endoscopic treatment tool 100 (also referred to as treatment tool 100) is a hemostatic forceps that cauterizes an affected area to stop bleeding. The treatment tool 100 includes a sheath 1, an operation wire 2 (see FIG. 5), a support member 3, forceps (jaws) 4 and an operation portion 5. In the following description, in the longitudinal axis direction A of the treatment tool 100, the side to be inserted into the patient's body is referred to as "distal end side A1", and the side of the operation portion 5 is referred to as "proximal end side A2".

[Sheath 1]

The sheath 1 is a flexible, elongated coil sheath extending from the distal end 1*a* to the proximal end 1*b*. The sheath 1 has an outer diameter that allows it to be inserted into channel 216 of endoscope 200. As shown in FIG. 1, when the sheath 1 is inserted into the channel 216, the distal end 1*a* of the sheath 1 can protrude from the distal end opening 212 of the channel 216. The sheath 1 may have insulating properties.

The proximal end 1*b* of the sheath 1 is connected to the operation portion 5 by a connecting portion 12 so as to be rotatable around the longitudinal axis.

[Operating Wire 2]

The operation wire 2 is inserted through the inner space 1*s* of the sheath 1. A distal end of the operating wire 2 is connected to the forceps 4, and a proximal end of the operating wire 2 is connected to the operation portion 5. The operation wire 2 is a metal wire 21 and a metal pipe 22 provided at the proximal end of the wire 21 (see FIG. 7). The wire 21 and the pipe 22 are fixed so as not to move relative to each other, for example, by chemical bonding such as adhesion or mechanical bonding such as caulking.

[Support Member 3]

The support member 3 is provided at the distal end 1*a* of the sheath 1 and supports the forceps 4 so that it can be opened and closed. The support member 3 may have a link mechanism that converts the forward/backward motion of the operation wire 2 into the opening/closing motion of the forceps 4.

[Forceps 4]

The forceps (jaws) 4 are members for grasping living tissue. The forceps 4 are supported by the support member 3 so as to be openable and closable toward the distal end side A1. The forceps 4 is made of a metal material such as stainless steel and includes a first forceps piece 41 and a second forceps piece 42. The support member 3 and the forceps 4 constitute a "treatment portion 110" for treating the affected area.

[Operation Portion 5]

Figure 3:
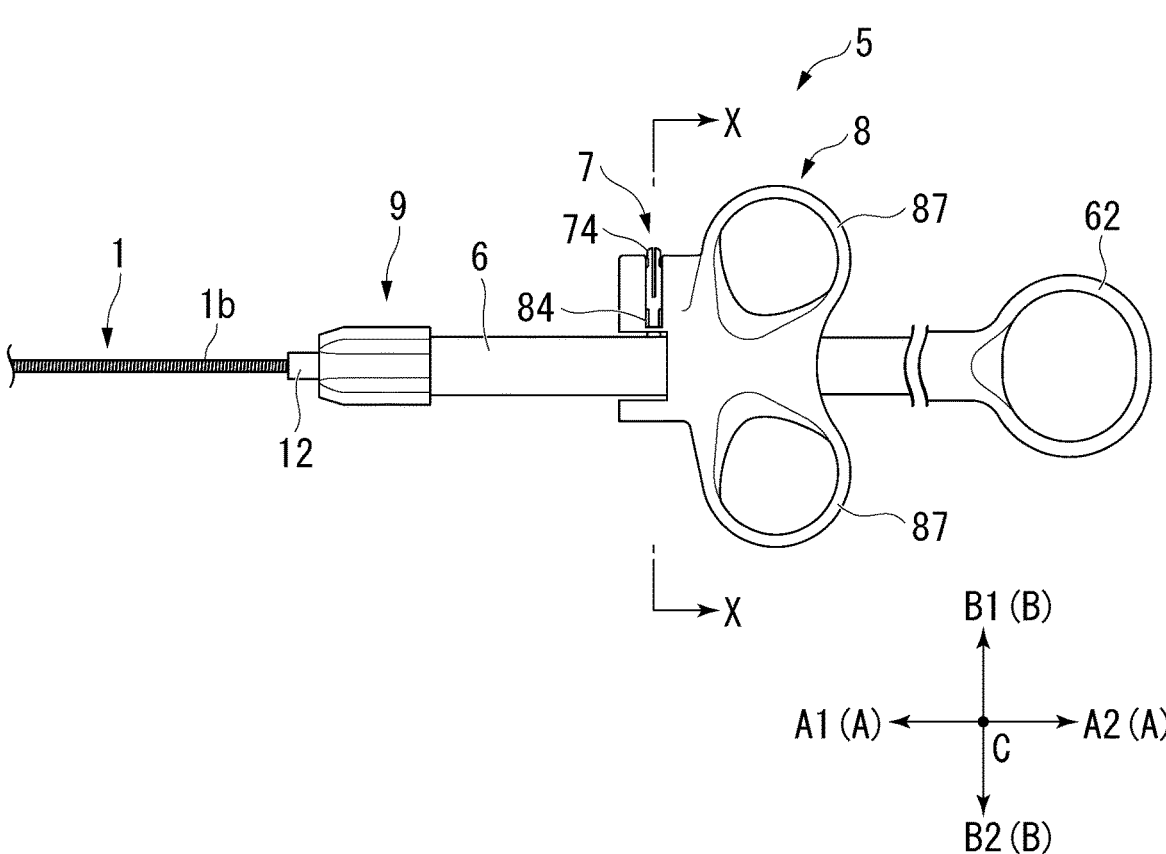
FIG. 3 is a side view of an operation portion of the endoscopic treatment tool.
Figure 4:
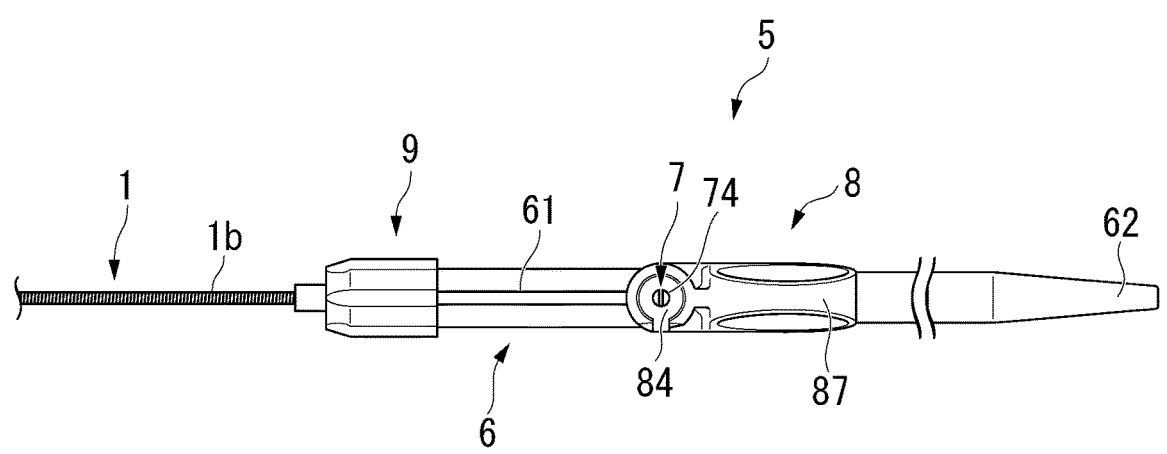
FIG. 4 is a top view of the operation portion.
Figure 4:
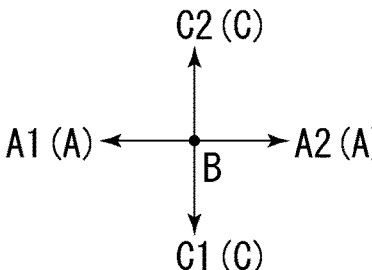

FIG. 3 is a side view of the operation portion 5. FIG. 4 is a top view of the operation portion 5.

The operation portion (handle) 5 is provided on the proximal end side A2 of the sheath 1. The operation portion 5 includes a handle body 6, a connector 7, a slider 8, and a rotating handle 9. In this embodiment the connector 7 is attached to the slider 8.

In the following description of the operation portion 5, the direction in which the connector 7 is provided with respect to the handle body 6 is defined as the upper side B1 in the vertical direction B, and the side opposite to the upper side B1 in the vertical direction B is defined as the "lower side B2". A direction perpendicular to the longitudinal direction A and the vertical direction B is defined as a "width direction C" or a "left-right direction C". The direction facing right when viewed from the distal side A1 to the proximal side A2 is defined as the "right side C1" in the width direction C, and the direction facing left is defined as the "left side C2" in the width direction C.

Figure 5:
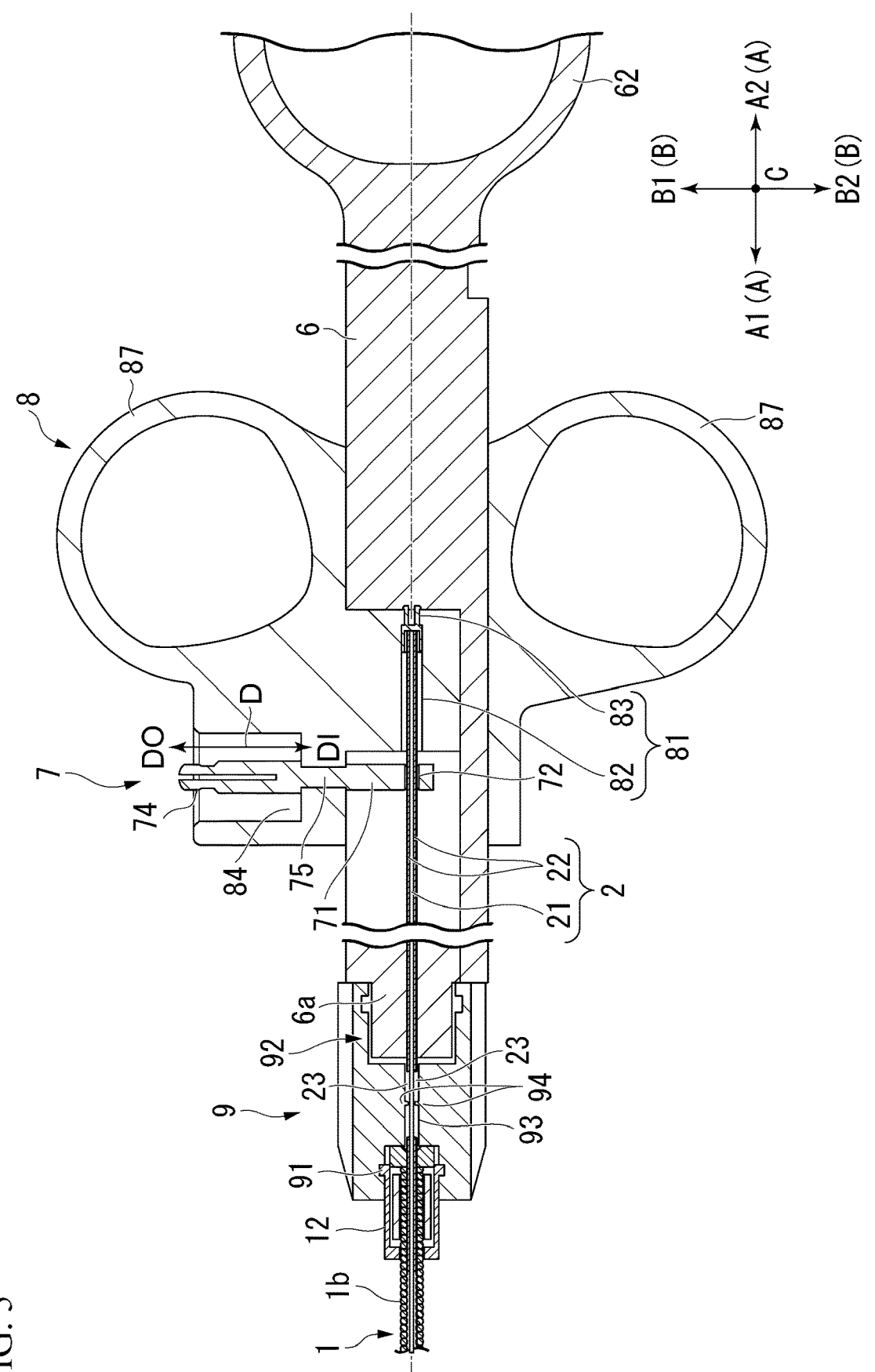
FIG. 5 is a cross-sectional view of the operation portion.

FIG. 5 is a cross-sectional view of the operation portion 5.

The handle body 6 has an internal space 6*s* through which the operation wire 2 can be inserted. The operating wire 2 passes through the inner space 1*s* of the sheath 1 and the inner space 6*s* of the handle body 6 and extends to the slider 8. The handle body 6 has a body slit 61 extending in the longitudinal direction A, as shown in FIG. 4. The body slit 61 communicates with the internal space 6*s*.

The handle body 6 has a thumb ring 62 on the proximal side A2. The operator can support the handle body 6 by inserting the thumb through the thumb ring 62.

The connector 7 can be connected to a high-frequency power supply (not shown) and is electrically and physically connected to the proximal end of the operation wire 2. The connector 7 can supply high-frequency current supplied from the high-frequency power supply to the forceps 4 via the operation wire 2.

The connector 7 is supported by the slider 8 and has a substantially columnar shape extending in the extension direction D. The extension direction D is a direction that intersects the longitudinal axis direction A, which is the advancing/retreating direction of the operation wire 2 and is a direction orthogonal to the longitudinal axis direction A in this embodiment. The connector 7 has a connecting portion 71, a conducting plug 74 and a reduced diameter portion 75.

Figure 6:
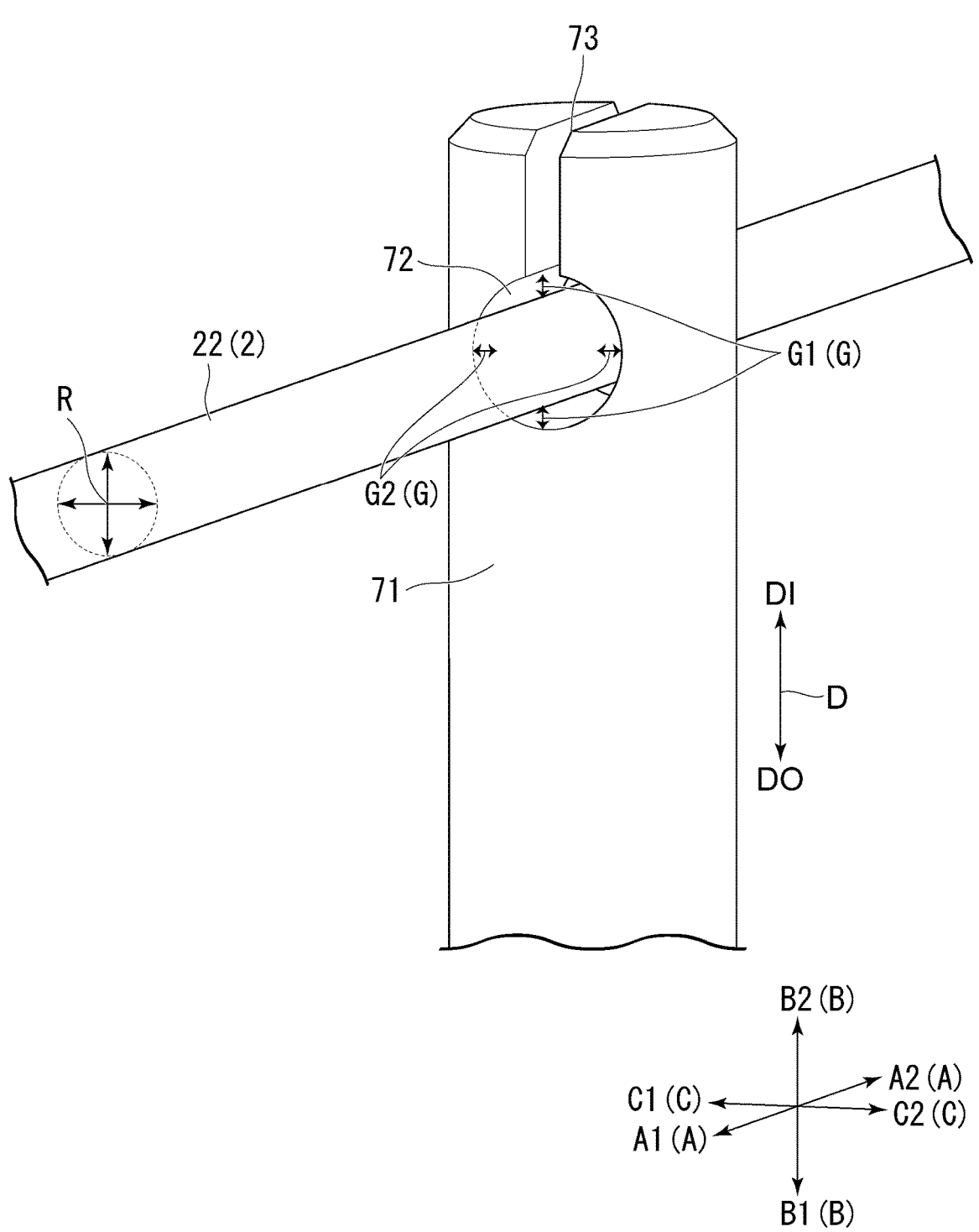
FIG. 6 is a diagram showing a connecting portion of a connector of the operation portion.

FIG. 6 is a diagram showing the connecting portion 71 of the connector 7.

The connecting portion 71 is formed in a substantially cylindrical shape and is provided on the inner side DI, which is one side in the extending direction D. The connecting portion 71 is inserted through the body slit 61 of the handle body 6 and connected to the operation wire 2. The connecting portion 71 has an insertion passage 72 and a slit 73.

Figure 7:
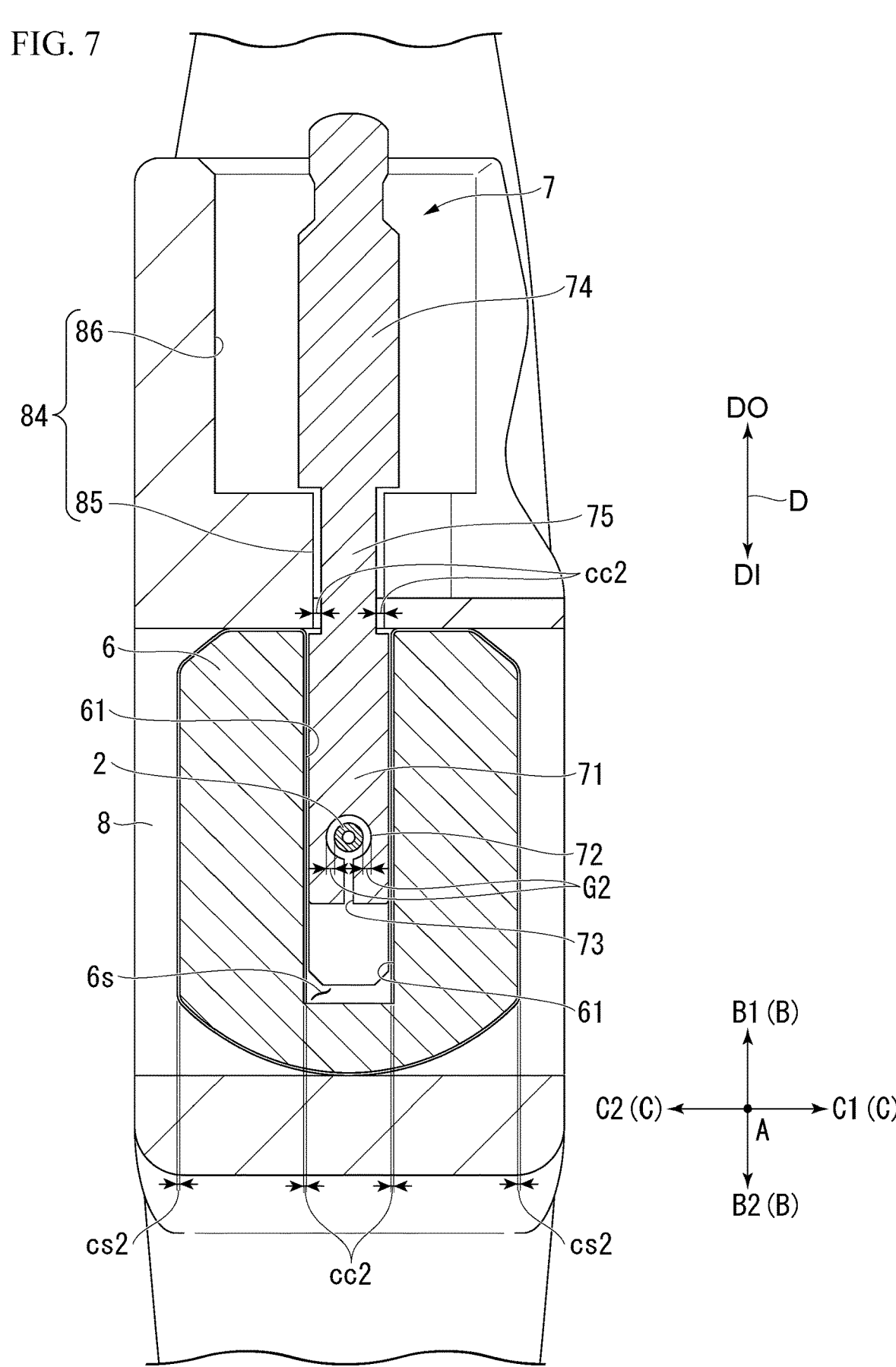
FIG. 7 is a cross-sectional view of the operation portion taken along line X-X of FIG. 3.

FIG. 7 is a cross-sectional view of the operation portion 5 taken along line X-X in FIG. 3.

The insertion passage 72 is a through-hole formed along the longitudinal direction A in which the operation wire 2 extends, and the pipe 22 provided at the proximal end portion of the operation wire 2 is inserted so as to advance and retreat. A gap G is provided between the inner peripheral surface of the insertion passage 72 and the operation wire 2. The gap G in the vertical direction B is referred to as "vertical gap G1", and the gap G in the horizontal direction C is referred to as "left and right gap G2".

The slit 73 is a slit extending from the insertion passage 72 to the end of the inner DI. The slit 73 is formed continuously from the distal end side A1 to the proximal end side A2 in the longitudinal axis direction A.

The conducting plug 74 is a plug provided on the outer side DO, which is the other side in the extending direction D and is connected with an A cord (active cord).

The reduced diameter portion 75 is an intermediate portion in the extending direction D and is provided between the insertion passage 72 and the conducting plug 74. The outer diameter of the reduced-diameter portion 73 is smaller than the outer diameter of the connecting portion 71 and the outer diameter of the conducting plug 74.

Figure 8:
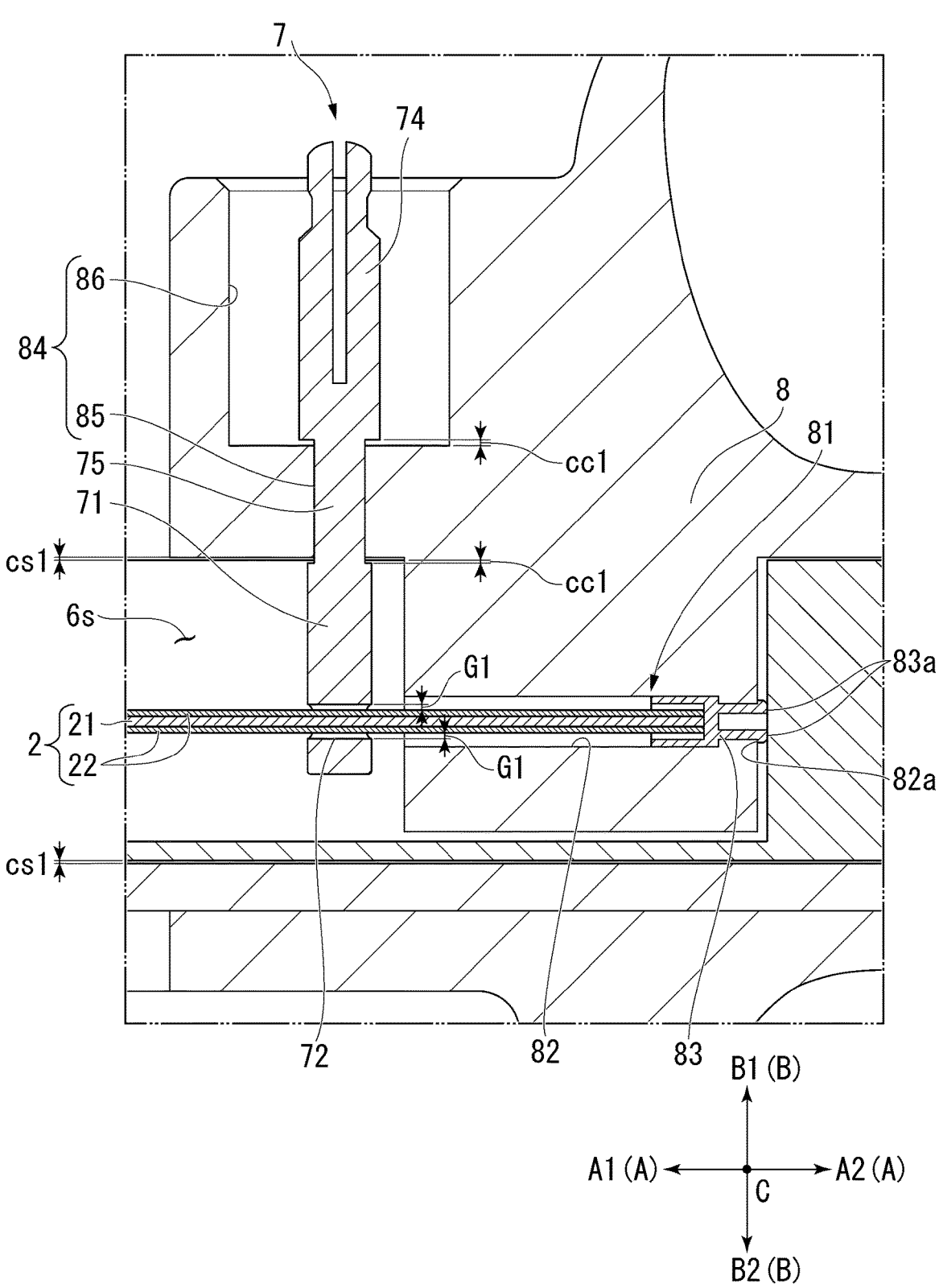
FIG. 8 is a cross-sectional view of a slider of the operation portion.

FIG. 8 is a cross-sectional view of the slider 8.

The slider 8 is attached so as to move back and forth along the body slit 61 of the handle body 6. The slider 8 can move back and forth along the longitudinal axis direction A with respect to the handle body 6 and cannot rotate about the longitudinal axis. A proximal end portion of the operation wire 2 is connected to the slider 8. The operating wire 2 advances and retreats when the operator advances and retreats the slider 8 relative to the handle body 6.

The slider 8 is attached to the handle body 6 so as to be able to advance and retreat. Therefore, as shown in FIG. 8, the slider 8 has a clearance (hereinafter also referred to as "vertical slider clearance CS1") in the vertical direction B between the slider 8 and the handle body 6. Further, as shown in FIG. 7, the slider 8 has a clearance (hereinafter also referred to as "left and right slider clearance CS2") in the left-right direction C between the slider 8 and the handle body 6.

The slider 8 has an operation wire support portion 81 that supports the operation wire 2, a connector support portion 84 that supports the connector 7, and double rings 87 provided on both sides in the vertical direction B.

The operation wire support portion 81 supports the proximal end portion of the operation wire 2. The operation wire support portion 81 has a first through hole 82 penetrating in the longitudinal direction A, and a connecting member 83 attached to a proximal end opening 82a of the first through hole 82.

The connecting member 83 is a member fixed to the proximal end of the operation wire 2, and has an elastic claw portion (snap fit) 83a on the proximal side A2. The connecting member 83 is fixed to the proximal end of the operation wire 2 by, for example, adhesion or press-fitting. The claw portion 83a engages with the edge of the proximal end opening 82a of the first through hole 82. The operation wire 2 (pipe 22) is attached to the slider 8 via the claw portion 83a so as to be unable to advance or retreat along the longitudinal axis direction A with respect to the slider 8 and to be rotatable about the longitudinal axis.

The connector support portion 84 supports the connector 7. The connector support portion 84 has a second through hole 85 penetrating in the vertical direction B and a cylindrical plug protection portion 86 formed on the upper side B1 of the second through hole 85.

The second through hole 85 is a through hole through which the reduced diameter portion 75 of the connector 7 is inserted. As shown in FIG. 8, the length in the vertical direction B of the second through hole 85 is shorter than the length in the vertical direction B of the reduced diameter portion 75. Therefore, the connector 7 has a clearance (hereinafter also referred to as "vertical connector clearance CC1") in the vertical direction B between itself and the slider 8.

As shown in FIG. 7, the length in the left-right direction C of the second through hole 85 is longer than the length in the left-right direction C of the reduced diameter portion 75 of the connector 7. Further, the length in the left-right direction C of the body slit 61 of the handle body 6 is longer than the length in the left-right direction C of the connecting portion 71 of the connector 7. Therefore, the connector 7 has a clearance in the left-right direction C between the handle body 6 and the slider 8 (hereinafter also referred to as "left-right connector clearance CC2").

Figure 9:
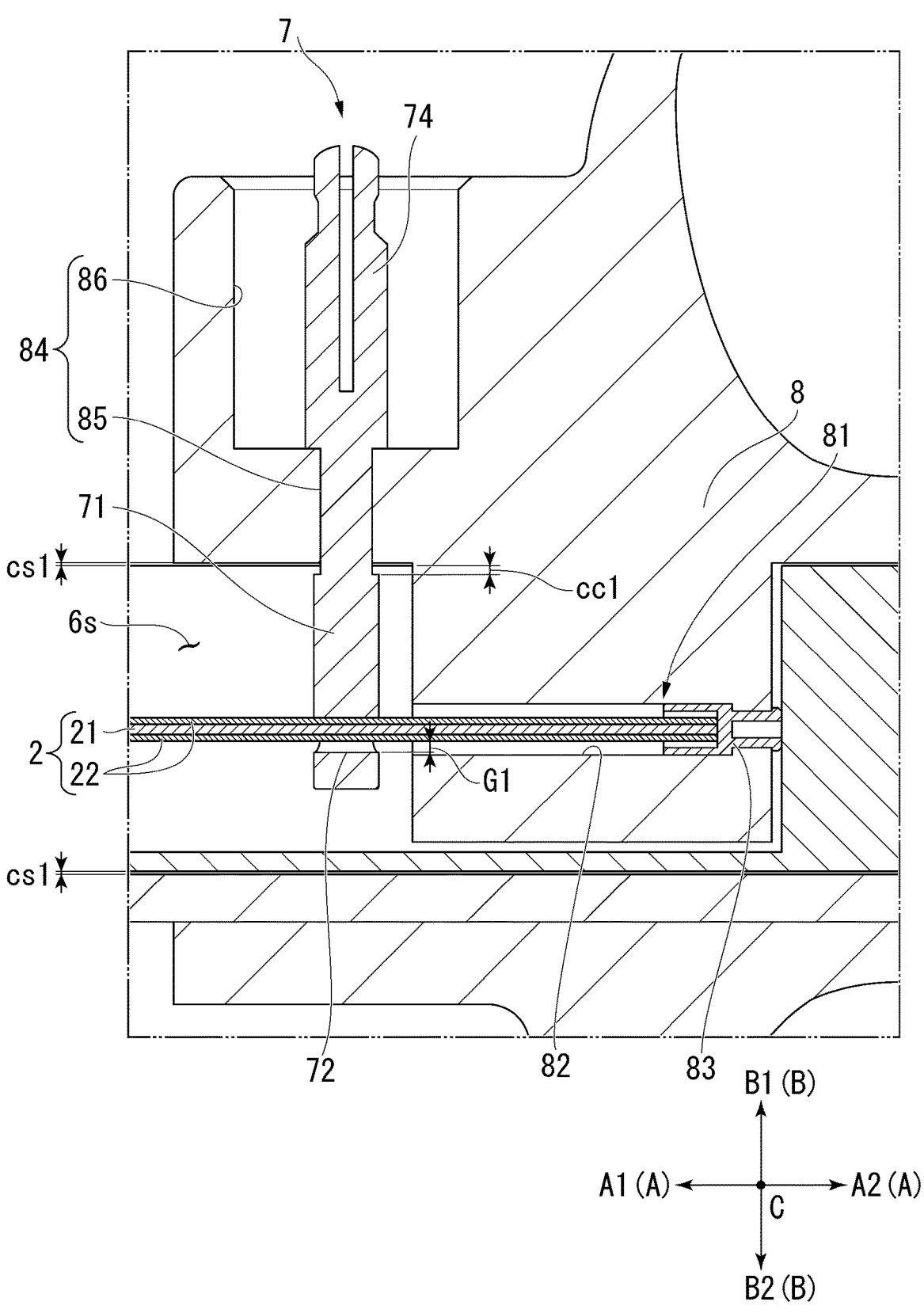
FIG. 9 is a cross-sectional view of the slider in which the lower side of the operation portion faces vertically downward.

FIG. 9 is a cross-sectional view of the slider 8 in which the lower side B2 of the operation portion 5 faces vertically downward.

When the lower side B2 of the operation portion 5 faces vertically downward (in the direction of gravity), since the connector 7 has a vertical connector clearance CC1, it moves downward B2 with respect to the handle body 6 as shown in FIG. 9. The vertical connector clearance CS1 is larger than the vertical gap G1. Therefore, the insertion passage 72 of the connector 7 contacts the operation wire 2 on the upper side B1 so as to be electrically conductive. That is, when the connector 7 moves in the first direction (lower side B2, inner side DI) in the radial direction R (see FIG. 6) of the operation wire 2, the insertion passage 72 electrically contacts the operation wire 2 in a second direction (upper side B1, outer side DO) opposite to the first direction.

Since the slider 8 that supports the connector 7 has a vertical slider clearance CS1, it moves downward B2 with respect to the handle body 6 as shown in FIG. 9. As a result, the connector 7 supported by the slider 8 also moves to the lower side B2 with respect to the handle body 6. Considering the vertical slider clearance CS1, if the sum of the vertical connector clearance CC1 and the vertical slider clearance CS1 is larger than the vertical gap G1, the insertion passage 72 of the connector 7 electrically contacts the operation wire 2 on the upper side B1. For example, when the vertical connector clearance CC1 is zero, the vertical slider clearance CS1 should be larger than the vertical gap G1.

Figure 10:
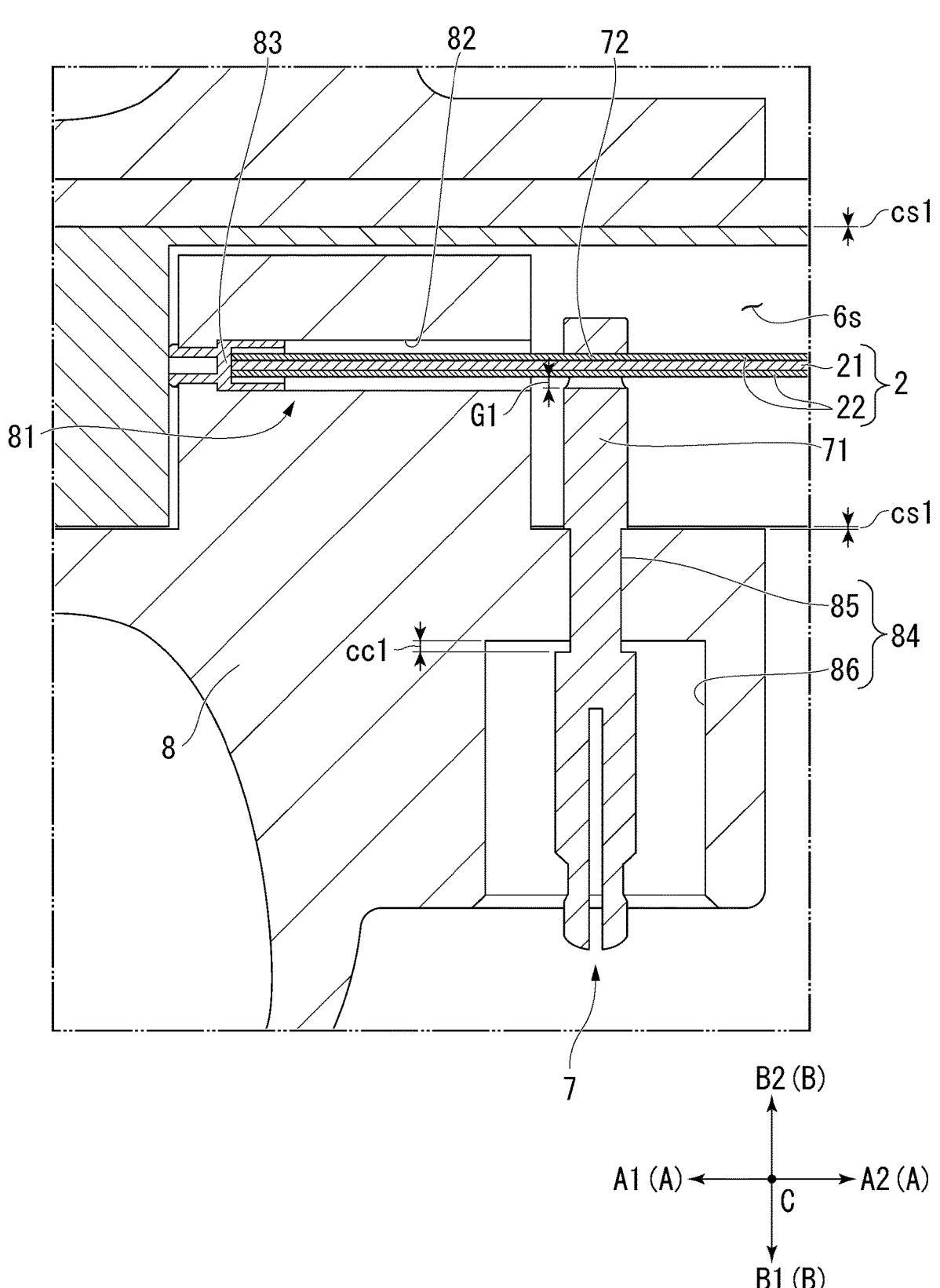
FIG. 10 is a cross-sectional view of the slider in which the upper side of the operation portion faces vertically downward.

FIG. 10 is a cross-sectional view of the slider 8 in which the upper side B1 of the operation portion 5 faces vertically downward.

When the upper side B1 of the operation portion 5 faces vertically downward, the connector 7 has a vertical connector clearance CC1, so that it moves to the upper side B1 with respect to the handle body 6 as shown in FIG. The vertical connector clearance CS1 is larger than the vertical gap G1. Therefore, the insertion passage 72 of the connector 7 electrically contacts the operation wire 2 on the lower side B2. That is, when the connector 7 moves in the second direction (upper side B1, outer side DO) in the radial direction R (see FIG. 6) of the operation wire 2, the insertion passage 72 electrically contacts the operation wire 2 in the first direction (lower side B2, inner side DI) opposite to the second direction.

Since the slider 8 that supports the connector 7 has a vertical slider clearance CS1, it moves upward B1 with respect to the handle body 6 as shown in FIG. 10. As a result, the connector 7 supported by the slider 8 also moves to the upper side B1 with respect to the handle body 6. Considering the vertical slider clearance CS1, if the total of the vertical connector clearance CC1 and the vertical slider clearance CS1 is larger than the vertical gap G1, the insertion passage 72 of the connector 7 is in contact with the operation wire 2 on the lower side B2 so as to be electrically conductive. For example, when the vertical connector clearance CC1 is zero, the vertical slider clearance CS1 should be larger than the vertical gap G1.

Figure 11:
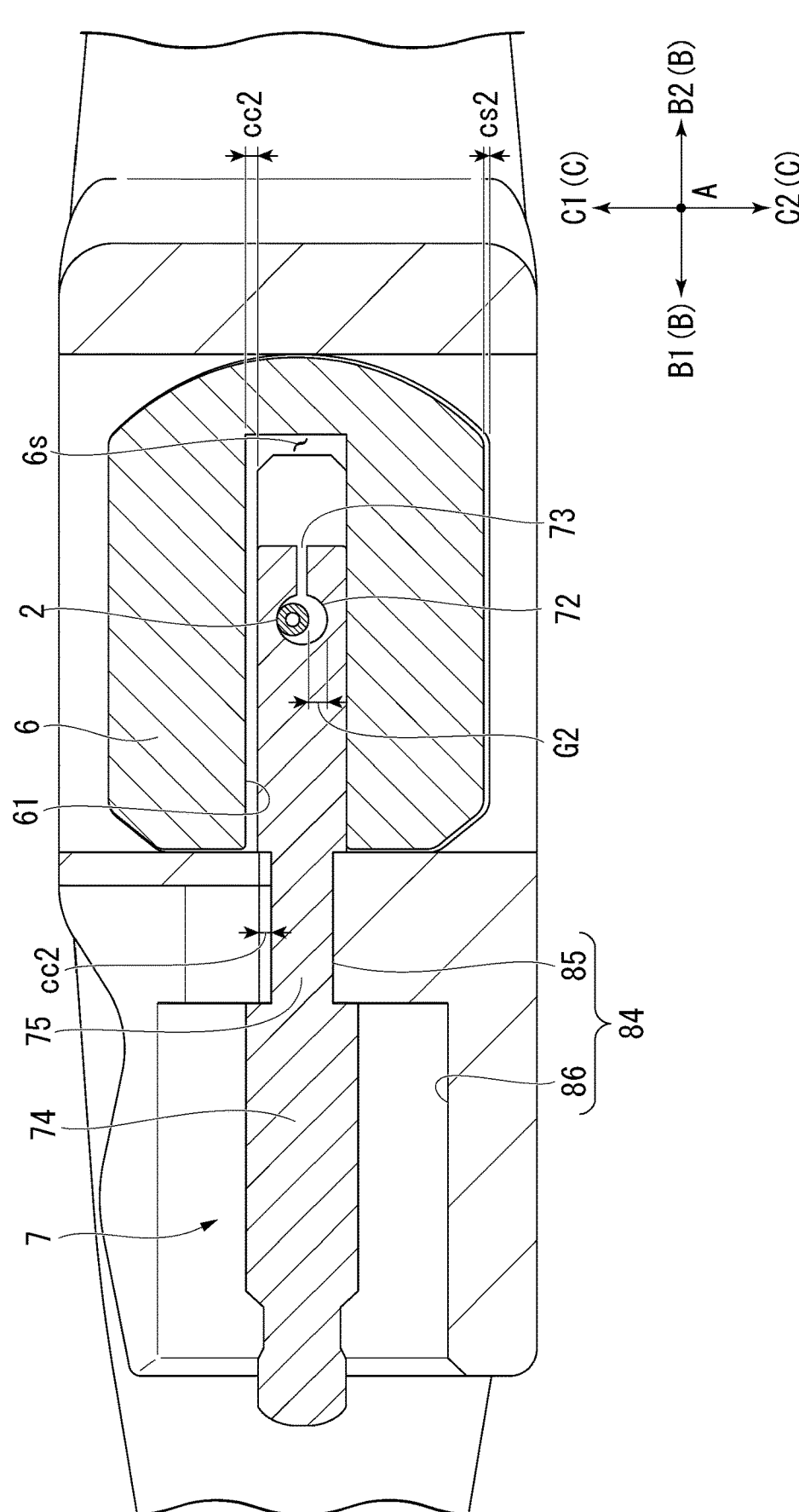
FIG. 11 is a cross-sectional view of the slider with the left side of the operation portion facing vertically downward.

FIG. 11 is a cross-sectional view of the slider 8 with the left side C2 of the operation portion 5 facing vertically downward.

When the left side C2 of the operation portion 5 faces vertically downward, the connector 7 has a left and right connector clearance CC2, so it moves to the left side C2 with respect to the handle body 6 as shown in FIG. 11. The left and right slider clearance CS2 is larger than the left and right gap G2. Therefore, the insertion passage 72 of the connector 7 contacts the operation wire 2 on the right side C1 so as to be electrically conductive. That is, when the connector 7 moves in the first direction (left side C2) in the radial direction R (see FIG. 6) of the operation wire 2, the insertion passage 72 electrically contacts the operation wire 2 in the second direction (right side C1) opposite to the first direction.

Since the slider 8 that supports the connector 7 has a left and right slider clearance CS2, it moves to the left side C2 with respect to the handle body 6 as shown in FIG. 11. As a result, the connector 7 supported by the slider 8 also moves to the left side C2 with respect to the handle body 6. Considering the left and right slider clearance CS2, if the sum of the left and right connector clearance CC2 and the left and right slider clearance CS2 is larger than the left and right gap G2, the insertion passage 72 of the connector 7 contacts the operation wire 2 on the right side C1 so as to be electrically conductive. For example, when the left-right connector clearance CC2 is zero, the left and right slider clearance CS2 should be larger than the left and right gap G2.

Similarly, when the right side C1 of the operation portion 5 faces vertically downward (the direction of gravity), when the connector 7 moves in the second direction (right side C1) in the radial direction R (see FIG. 6) of the operation wire 2, the insertion passage 72 electrically contacts the operation wire 2 in the first direction (left side C2) opposite to the second direction.

Similarly, in a case where the direction perpendicular to the longitudinal axis direction A of the operation portion 5 and other than the vertical direction B and the horizontal direction C faces vertically downward, when the connector 7 moves in the first direction in the radial direction R (see FIG. 6) of the operation wire 2, the insertion passage 72 electrically contacts the operation wire 2 in the second direction opposite to the first direction. When the connector 7 moves in the second direction in the radial direction R (see FIG. 6) of the operation wire 2, the insertion passage 72 electrically contacts the operation wire 2 in the first direction. That is, no matter which direction the operation portion 5 is tilted, a portion of the insertion passage 72 is always in electrical contact with the operating wire 2.

As shown in FIG. 5, the rotary handle 9 is provided on the handle body 6 on the distal end side A1 from the slider 8. The rotary handle 9 cannot advance or retreat along the longitudinal axis direction A with respect to the handle body 6 and is rotatable about the longitudinal axis. The rotating handle 9 includes a sheath supporting portion 91 that supports the connecting portion 12 of the sheath 1, a rotating connecting portion 92 that is connected to the handle body 6 so as to be rotatable about the longitudinal axis, an insertion hole 93 through which the operation wire 2 is inserted, and a wire driving portion 94 that drives the operation wire 2 to rotate.

The rotary connecting portion 92 is a concave portion recessed toward the distal end side A1 on the proximal end side A2 of the rotary handle 9. The rotary connecting portion 92 is attached to the distal end portion 6a of the handle body 6 so as to be rotatable around the longitudinal axis.

The through-hole 93 is a through-hole formed along the rotation axis of the rotary handle 9. The operation wire 2 can move forward and backward along the longitudinal axis direction A inside the insertion hole 93 and can rotate about the longitudinal axis.

As shown in FIG. 5, the wire driving portion 94 is a convex portion protruding radially inward from the inner peripheral surface of the insertion hole 93. The wire driving portions 94 are formed on both sides of the rotation shaft of the rotary handle.

Figure 12:
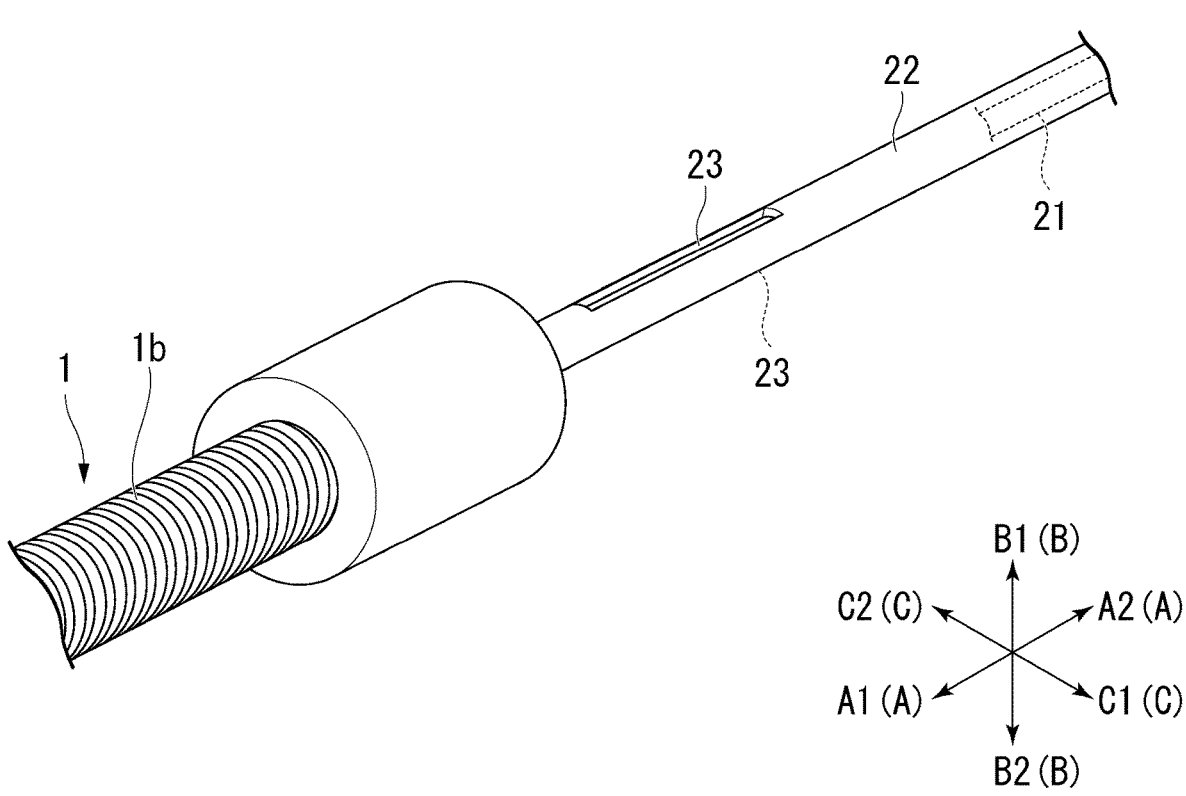
FIG. 12 is a diagram showing slits formed in a pipe of an operation wire.

FIG. 12 is a diagram showing the slits 23 formed in the pipe 22.

The wire driving portion 94 engages with the slit 23 formed in the pipe 22. The slit 23 is a recess extending along the longitudinal axis direction A. The slits 23 are formed on both sides of the wire 21. The pipe 22 can advance and retreat along the longitudinal axis direction A with respect to the wire driving portion 94 of the rotating handle 9 and cannot rotate about the longitudinal axis with respect to the wire driving portion 94 of the rotating handle 9. When the rotary handle 9 rotates about the longitudinal axis, the wire driving section 94 rotates the slit 23 about the longitudinal axis, thereby rotating the operation wire 2 about the longitudinal axis.

The length of the slit 23 in the longitudinal direction A is longer than the length in which the slider 8 can advance and retreat in the longitudinal direction A. Therefore, even when the operation wire 2 moves back and forth due to the forward and backward movement of the slider 8, the wire driving portion 94 is positioned inside the slit 23, so that the wire driving portion 94 is maintained in a state in which the operation wire 2 can be driven to rotate.

[How to Use the Endoscope Treatment System 300]

Next, a procedure (a method of using the endoscopic treatment system 300) using the endoscopic treatment system 300 of this embodiment will be described. Specifically, incision/ablation of a lesion and hemostasis in endoscopic therapy such as ESD (endoscopic submucosal dissection) will be described.

Bleeding often accompanies incision and ablation treatments. If bleeding occurs, the operator will stop the bleeding. Hemostasis treatment is a treatment to cauterize an ulcer, an incision, or a bleeding site that bleeds during the ablation treatment after exfoliating a lesion to stop bleeding.

The operator rotates the rotation handle 9 to rotate the operation wire 2 and the forceps 4 in order to place the forceps 4 at an appropriate treatment position. Since the connector 7 does not rotate even when the rotating handle 9 rotates, the A cord (active cord) connected to the connector 7 does not get entangled with the operation portion 5.

The operator energizes the operation wire 2 with a high-frequency current. At least a portion of the insertion passage 72 is in contact with the operation wire 2 in an electrically conductive manner regardless of which direction of the direction perpendicular to the longitudinal axis direction A of the operation portion 5 faces vertically downward. Therefore, high-frequency current is applied from the connector 7 to the operation wire 2 regardless of the posture of the operation portion 5, and the forceps 4 can cauterize the bleeding site.

The operator continues the above operations (treatment) as necessary, finally excises the lesion, and ends the ESD procedure.

According to the endoscopic treatment tool 100 according to the present embodiment, the connector 7 supplied with high-frequency current does not rotate, and the A cord (active cord) connected to the connector 7 does not get entangled with the operation portion 5. Moreover, the connector 7 and the operation wire 2 are preferably connected regardless of the posture of the operation portion 5.

As described above, the first embodiment of the present invention has been described in detail with reference to the drawings, but the specific configuration is not limited to this embodiment, and design changes and the like are included within the scope of the present invention. Also, the constituent elements shown in the above-described embodiment and modification can be combined as appropriate.

In the above embodiment, the treatment portion 110 is a hemostatic forceps that cauterizes the affected area to stop bleeding, but the type of treatment portion is not limited to this. The treatment tool may be any high-frequency treatment device for applying high-frequency current, and may be, for example, a high-frequency knife.

Figure 13:
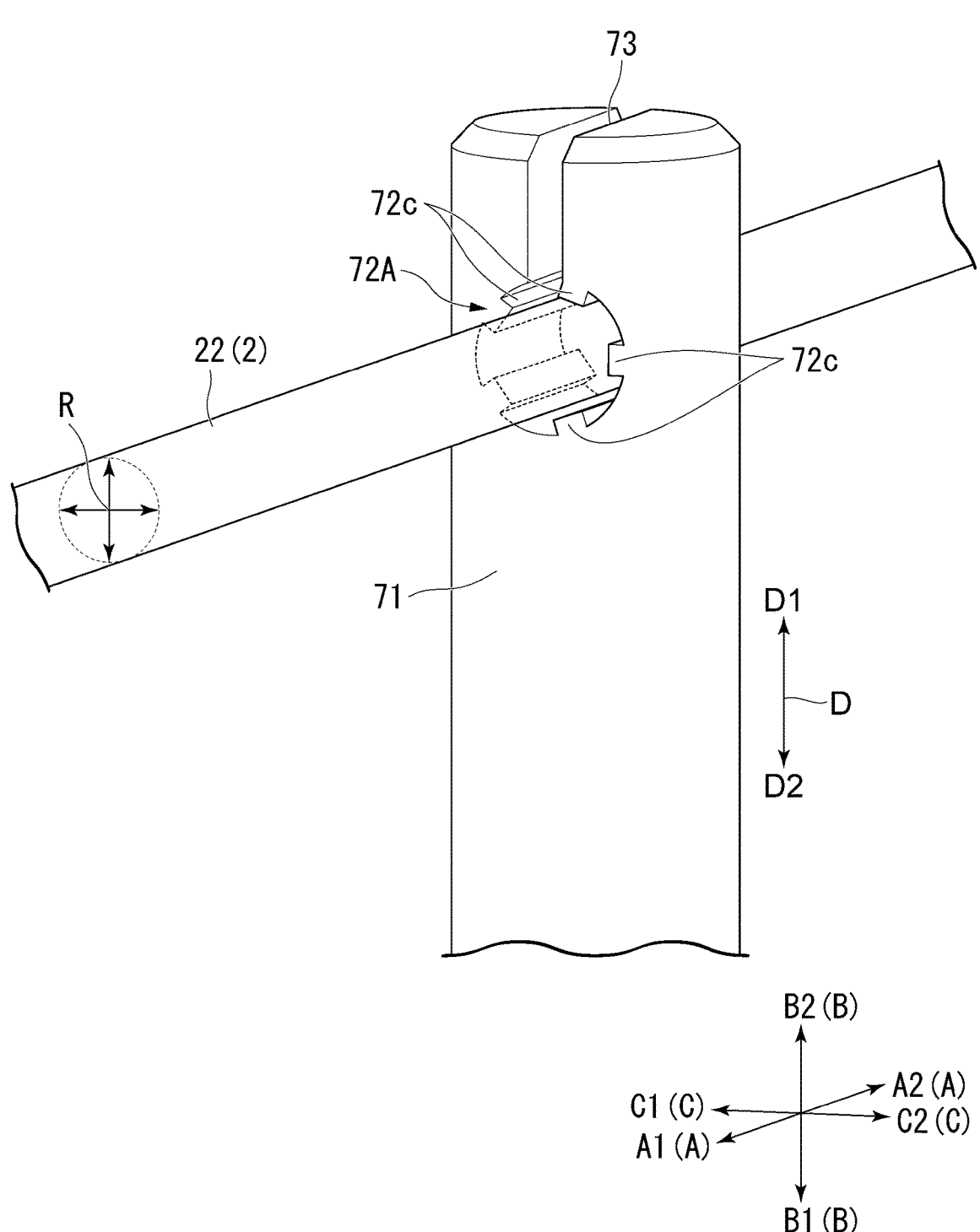
FIG. 13 is a diagram showing a modified example of an insertion passage of the connector.

FIG. 13 is a diagram showing an insertion passage 72A that is a modification of the insertion passage 72.

The insertion passage 72A has ribs 72c protruding inward in the radial direction R from the inner peripheral surface. The rib 72c extends in the longitudinal direction A. By adjusting the size of the rib 72c, the contact area between the insertion passage 72A and the operation wire 2 can be adjusted.

Second Embodiment

An endoscope treatment tool 100B according to a second embodiment of the present invention will be described with reference to FIGS. 14 to 16. In the following description, the same reference numerals are given to the configurations as those already described, and redundant descriptions will be omitted.

[Treatment Tool for Endoscope 100B]

The endoscopic treatment tool 100B (also referred to as the treatment tool 100B) is a hemostatic forceps that cauterizes the affected area to stop bleeding. The treatment tool 100B includes a sheath 1, an operation wire 2, a support member 3, forceps (jaws) 4, and an operation portion 5B.

Figure 14:
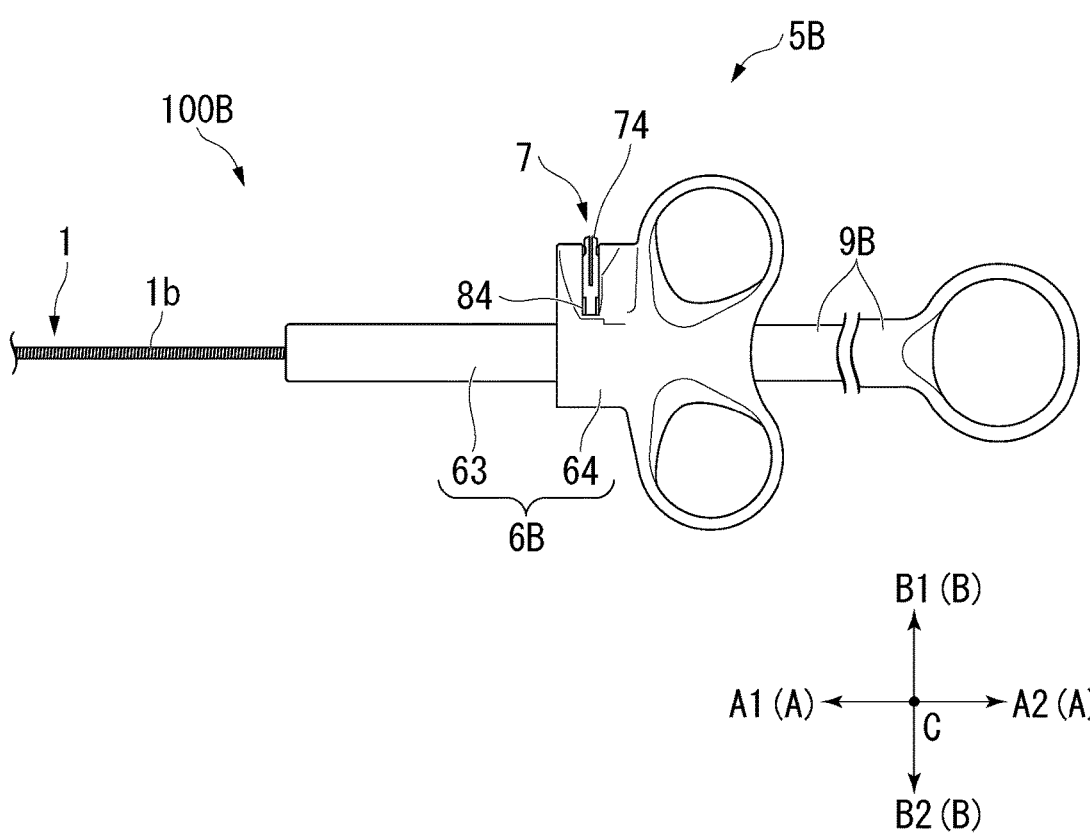
FIG. 14 is a diagram showing an operation portion of an endoscope treatment tool according to a second embodiment.

FIG. 14 is a diagram showing the operation portion 5B.

The operation portion 5B is provided on the proximal end side A2 of the sheath 1. The operation portion 5B includes a handle body 6B, a connector 7, and a rotating handle 9B. In this embodiment, the connector 7 is attached to the handle body 6B.

Figure 15:
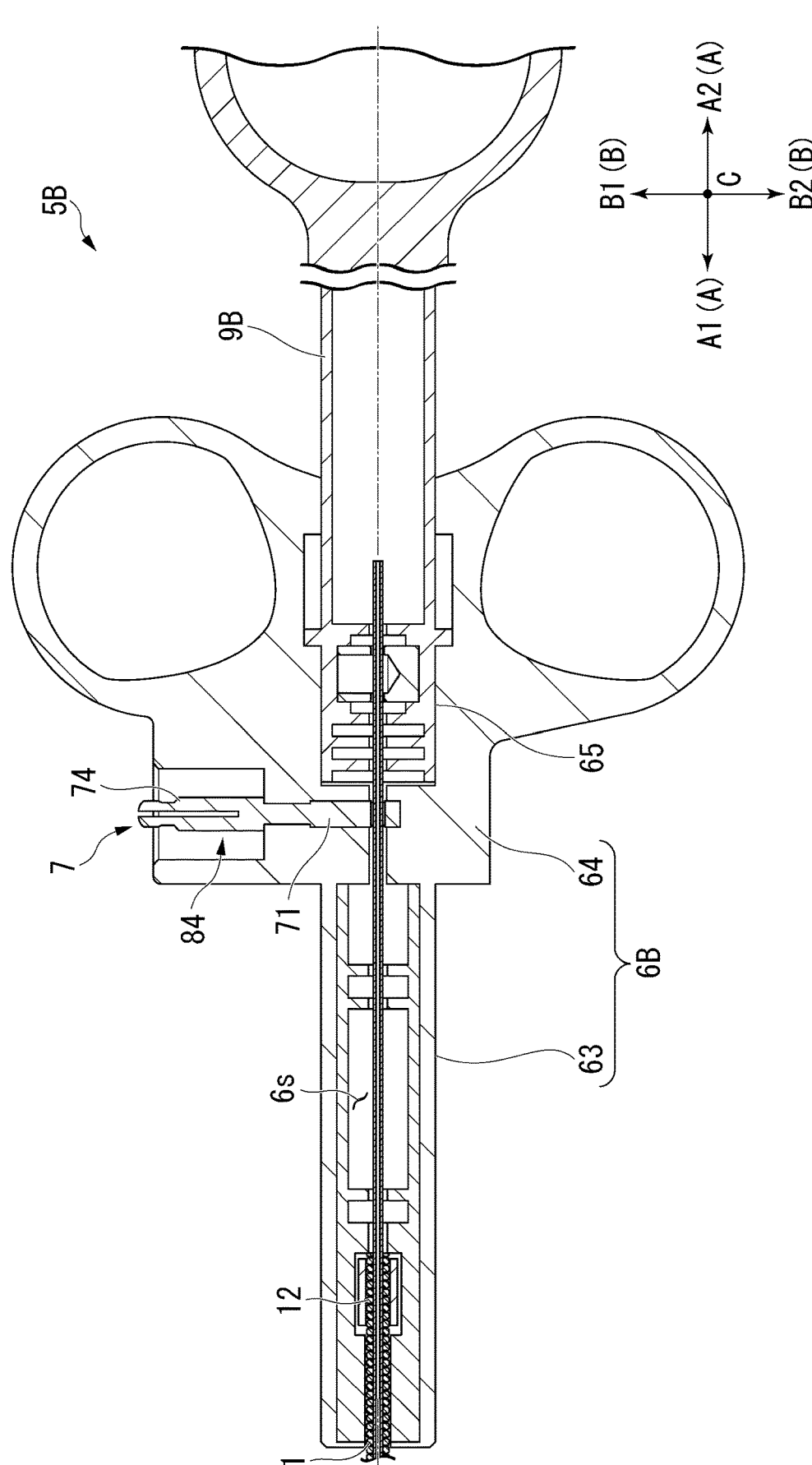
FIG. 15 is a cross-sectional view of the operation portion.

FIG. 15 is a cross-sectional view of the operation portion 5B.

The handle body 6B has a cylindrical portion 63, a fixed slider 64, and a rotating handle support portion 65. The cylindrical portion 63 is formed in a substantially tubular shape and has an internal space 6s through which the operation wire 2 is inserted. The connecting portion 12 that connects the proximal end 1b of the sheath 1 so as to be rotatable around the longitudinal axis is housed on the cylindrical portion 63 side.

The fixed slider 64 has the shape as the slider 8 of the first form. The fixed slider 64 is formed integrally with the cylindrical portion 63 and is part of the handle body 6B. Therefore, unlike the slider 8 of the first embodiment, the fixed slider 64 cannot advance or retreat along the longitudinal axis direction A.

Figure 16:
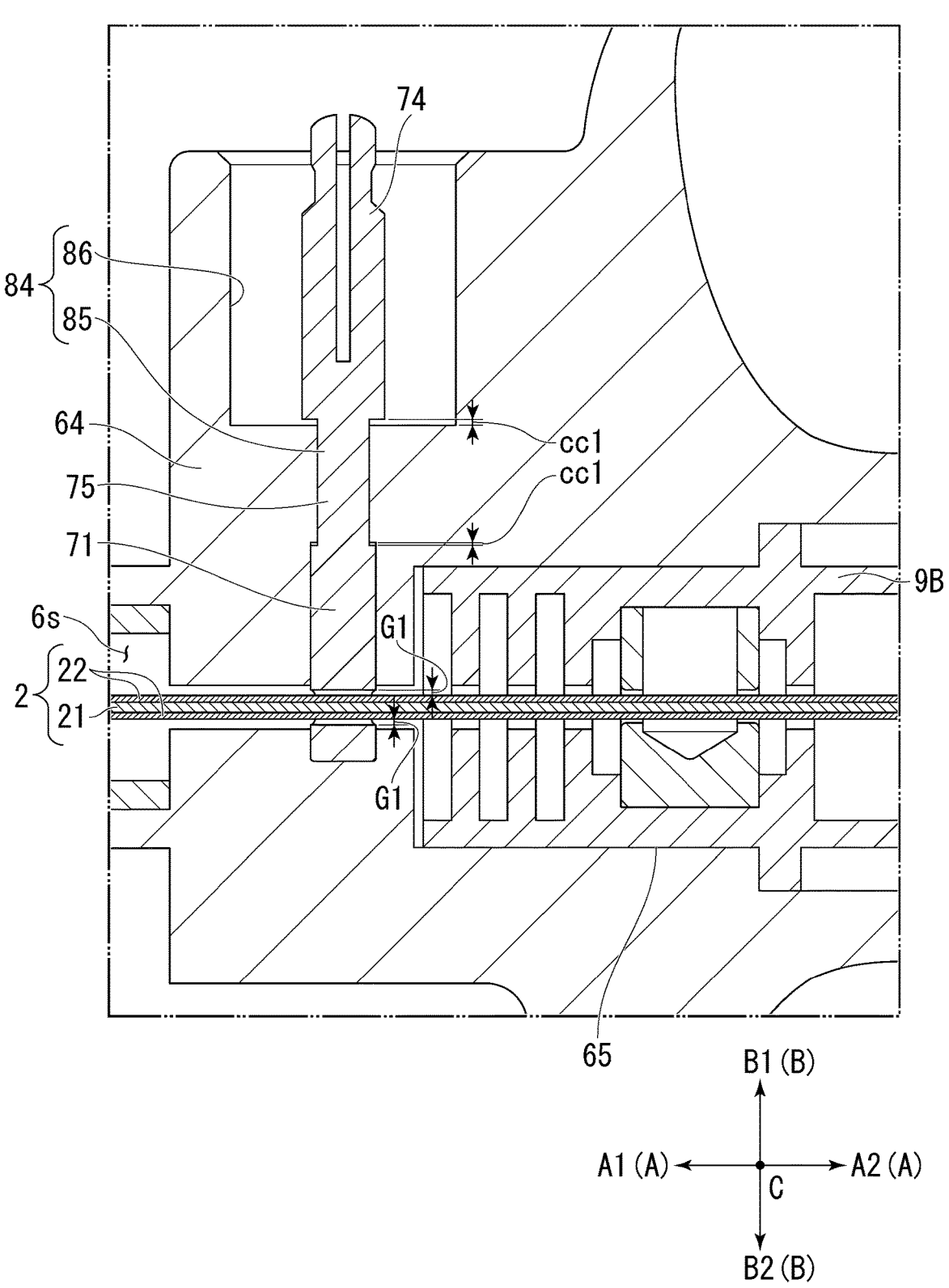
FIG. 16 is a cross-sectional view of a fixed slider of the operation portion.

FIG. 16 is a cross-sectional view of the fixed slider 64.

The fixed slider 64 has a connector support portion 84 similar to the slider 8 of the first embodiment. The connector 7 has a vertical connector clearance CC1 in the vertical direction B between it and the fixed slider 64. In addition, the connector 7 has a left-right connector clearance CC2 in the left-right direction C between the fixed slider 64 and the fixed slider 64.

As in the first embodiment, the vertical connector clearance CC1 is larger than the vertical gap G1. Also, the left-right connector clearance CC2 is larger than the left and right gap G2. Therefore, when the connector 7 moves in the first direction in the radial direction R (see FIG. 6) of the operation wire 2, the insertion passage 72 electrically contacts the operation wire 2 in the second direction opposite to the first direction. When the connector 7 moves in the second direction in the radial direction R (see FIG. 6) of the operation wire 2, the insertion passage 72 electrically contacts the operation wire 2 in the first direction.

The rotary handle support portion 65 is provided on the proximal end side A2 of the fixed slider 64 and supports the rotary handle 9B so as to be able to advance and retreat along the longitudinal axis direction A and to be rotatable around the longitudinal axis.

The rotary handle 9B is supported by the rotary handle support portion 65 of the handle body 6B. The rotary handle 9B can advance and retreat along the longitudinal axis direction A with respect to the handle body 6 and can rotate about the longitudinal axis.

The proximal end of the operation wire 2 is fixed to the rotating handle 9B. The proximal end of the operation wire 2 is fixed to the rotary handle 9B by chemical bonding such as adhesion or mechanical bonding such as caulking. By moving the rotating handle 9B forward and backward along the longitudinal axis direction A, the operation wire 2 is moved forward and backward. The operation wire 2 is rotated by rotating the rotating handle 9B around the longitudinal axis.

According to the endoscopic treatment tool 100B according to this embodiment, the connector 7 supplied with high-frequency current does not rotate, and the A cord (active cord) connected to the connector 7 does not get entangled with the operation portion 5B. Moreover, the connector 7 and the operation wire 2 are preferably connected regardless of the posture of the operation portion 5B.

When the sheath 1 is made of a conductive material, a configuration may be adopted in which the sheath 1 is extended to the position of the connector 7 so that the connector 7 and the sheath 1 are brought into contact with each other and the connector 7 and the sheath 1 are electrically connected instead of the operation wire 2.

As described above, the second embodiment of the present invention has been described in detail with reference to the drawings, but the specific configuration is not limited to this embodiment, and design changes and the like are also included within the scope of the present invention. Also, the constituent elements shown in the above-described embodiment and modification can be combined as appropriate.

Third Embodiment

An endoscope treatment tool 100C according to a second embodiment of the present invention will be described with reference to FIGS. 17 to 21. In the following description, the same reference numerals are given to the configurations as those already described, and redundant descriptions will be omitted.

[Treatment Tool for Endoscope 100C]

The endoscopic treatment tool 100C (also referred to as the treatment tool 100C) is a high-frequency knife. The treatment tool 100B includes a sheath 1, an operation wire 2, a knife 4C, and an operation portion 5C.

Figure 17:
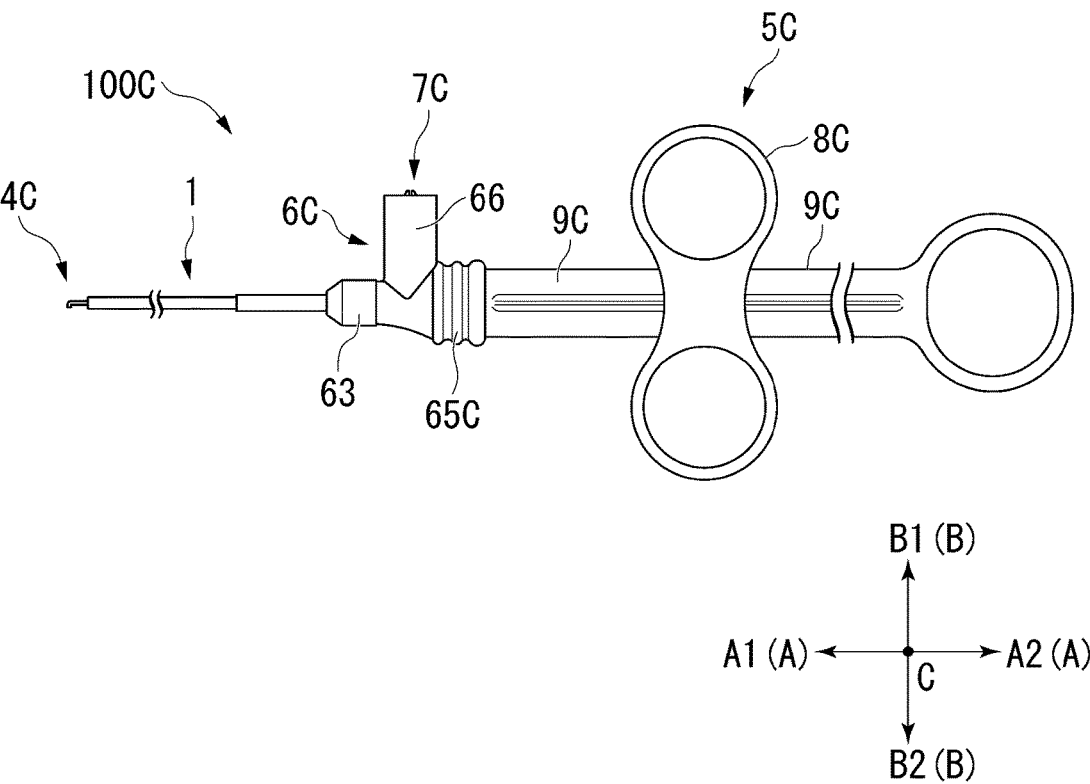
FIG. 17 is a diagram showing an operation portion of an endoscope treatment tool according to a third embodiment.

FIG. 17 is a diagram showing the operation portion 5C.

The operation portion 5C is provided on the proximal side A2 of the sheath 1. The operation portion 5C includes a handle body 6C, a connector 7C, a slider 8C, and a rotary handle 9C. In this embodiment, the connector 7C is attached to the handle body 6C.

Figure 18:
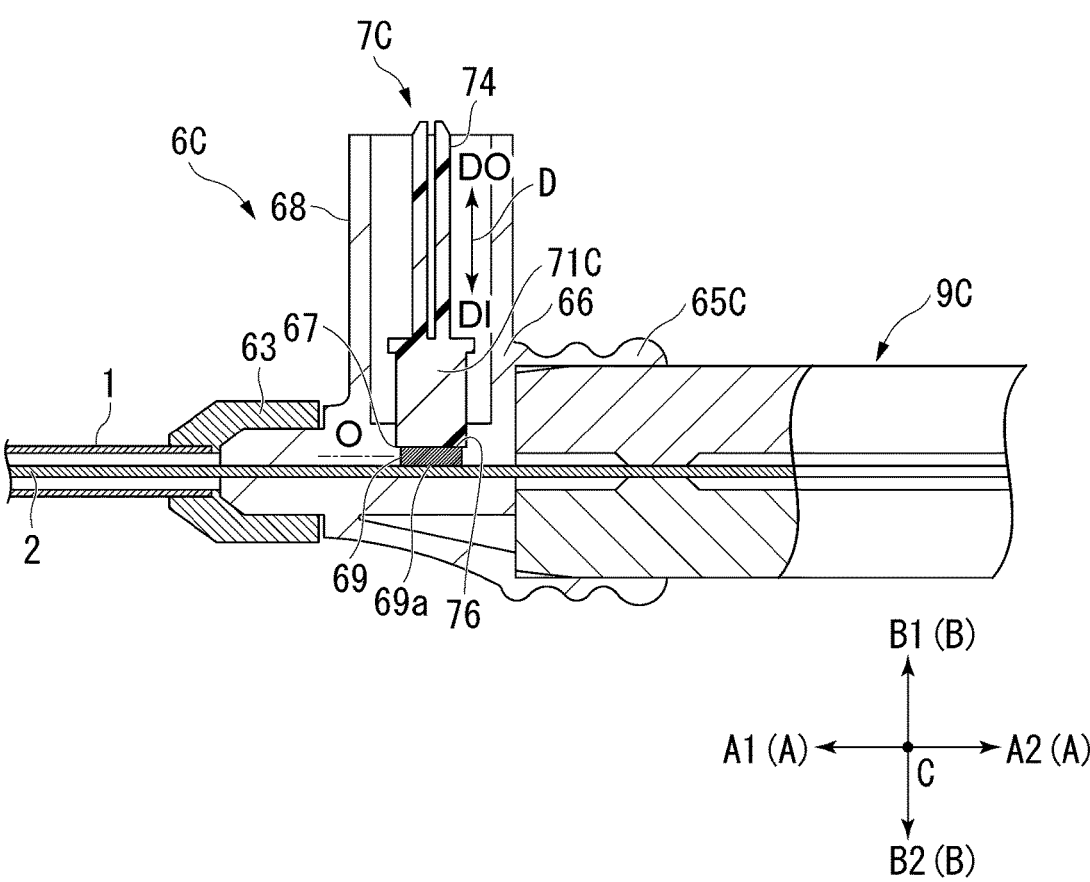
FIG. 18 is a cross-sectional view of a handle body of the operation portion.

FIG. 18 is a cross-sectional view of the handle body 6C.

The handle body 6C has a cylindrical portion 63, a rotary handle support portion 65C, and a connector support portion 66.

The rotating handle support portion 65C is provided on the proximal end side A2 of the handle body 6C, and supports the rotating handle 9C so that it can advance and retreat along the longitudinal axis direction A and cannot rotate around the longitudinal axis.

The connector support portion 66 supports the connector 7C. The connector support portion 66 includes a third through hole 67 through which the connector 7C penetrates in the vertical direction B, a cylindrical plug protection portion 68 formed on the upper side B1 of the third through hole 67, and a conductive member 69.

The conductive member 69 is formed in a substantially columnar shape from a conductive material. The conductive member 69 is a member that electrically and physically connects the operation wire 2 and the connector 7C and is arranged between the operation wire 2 and the connector 7C. The conductive member 69 is arranged such that the central axis O of the conductive member 69 extends along the longitudinal axis direction A. Further, the conductive member 69 is supported so as to be rotatable around the central axis O.

The conductive member 69 has a pressing area 69a that directly presses the pipe 22 of the operation wire 2. The pressing area 69a is curved but may be flat. The conductive member 69 is formed in a substantially columnar shape, and the pressing area 69a is formed in a shape that allows easy contact with the operation wire 2. Therefore, even when the operation wire 2 rotates around the longitudinal axis, the connector 7C and the operation wire 2 are preferably connected.

The connector 7C can be connected to a high-frequency power supply (not shown), and is electrically and physically connected to the proximal end of the operation wire 2 via the conductive member 69. The connector 7C can supply high-frequency current supplied from the high-frequency power supply to the knife 4C via the operation wire 2.

The connector 7C is supported by the connector support portion 66 of the handle body 6C and has a substantially columnar shape extending in the extension direction D. The extension direction D is a direction that intersects the longitudinal axis direction A, which is the advancing/retreating direction of the operation wire 2 and is a direction orthogonal to the longitudinal axis direction A in this embodiment. The connector 7C has a connecting portion 71C and a conducting plug 74.

The connecting portion 71C is formed in a substantially cylindrical shape and is provided on the inner side DI, which is one side in the extending direction D. The connecting portion 71C is inserted through the third through hole 67 and contacts the conductive member 69 at the end portion 76 of the inner DI.

The conducting plug 74 is a plug provided on the outer side DO, which is the other side in the extending direction D and is connected with an A cord (active cord).

The rotary handle 9C is supported by the rotary handle support portion 65C of the handle body 6C. The rotating handle 9C cannot advance or retreat along the longitudinal axis direction A with respect to the handle body 6C and can rotate about the longitudinal axis.

The rotary handle 9C has a slit-shaped slider support portion 95 that supports the slider 8C so that it can advance and retreat along the longitudinal axis direction A.

The slider 8C is attached so as to move back and forth along the slider support portion 95 of the rotary handle 9C. The slider 8C can advance and retreat along the longitudinal axis direction A with respect to the rotary handle 9C and cannot rotate about the longitudinal axis. A proximal end portion of the operation wire 2 is connected to the slider 8C. The operating wire 2 advances and retreats when the operator advances and retreats the slider 8 relative to the handle body 6.

According to the endoscopic treatment tool 100C according to this embodiment, the connector 7C to which the high-frequency current is supplied does not rotate, and the A cord (active cord) connected to the connector 7C does not get entangled with the operation portion 5C. Moreover, the connector 7C and the operation wire 2 are preferably connected regardless of the posture of the operation portion 5C.

As described above, the third embodiment of the present invention has been described in detail with reference to the drawings, but the specific configuration is not limited to this embodiment, and design changes and the like are included within the scope of the present invention. Also, the constituent elements shown in the above-described embodiment and modification can be combined as appropriate.

(Modification)

Figure 19:
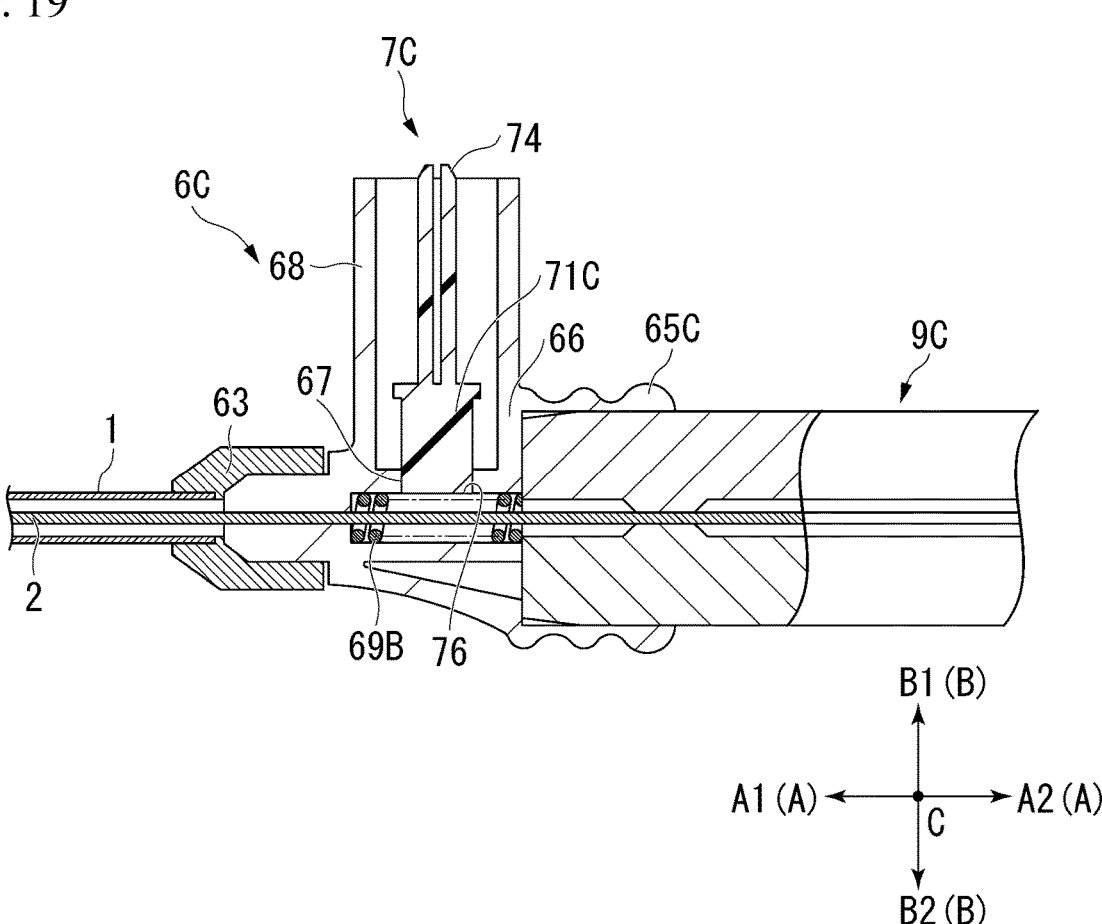
FIG. 19 is a diagram showing a modification of the conductive member of the handle body.

In the above embodiment, the conductive member 69 is a columnar member, but the mode of the conductive member is not limited to this. FIG. 19 shows a conductive member 69B that is a modification of the conductive member 69. The conductive member 69B is a coil spring made of metal and is wound around the outer peripheral portion of the operation wire 2. The conductive member 69B has elasticity, and even when the connector 7C moves back and forth in the extension direction D, the connector 7C and the operation wire 2 are preferably connected.

(Modification)

Figure 20:
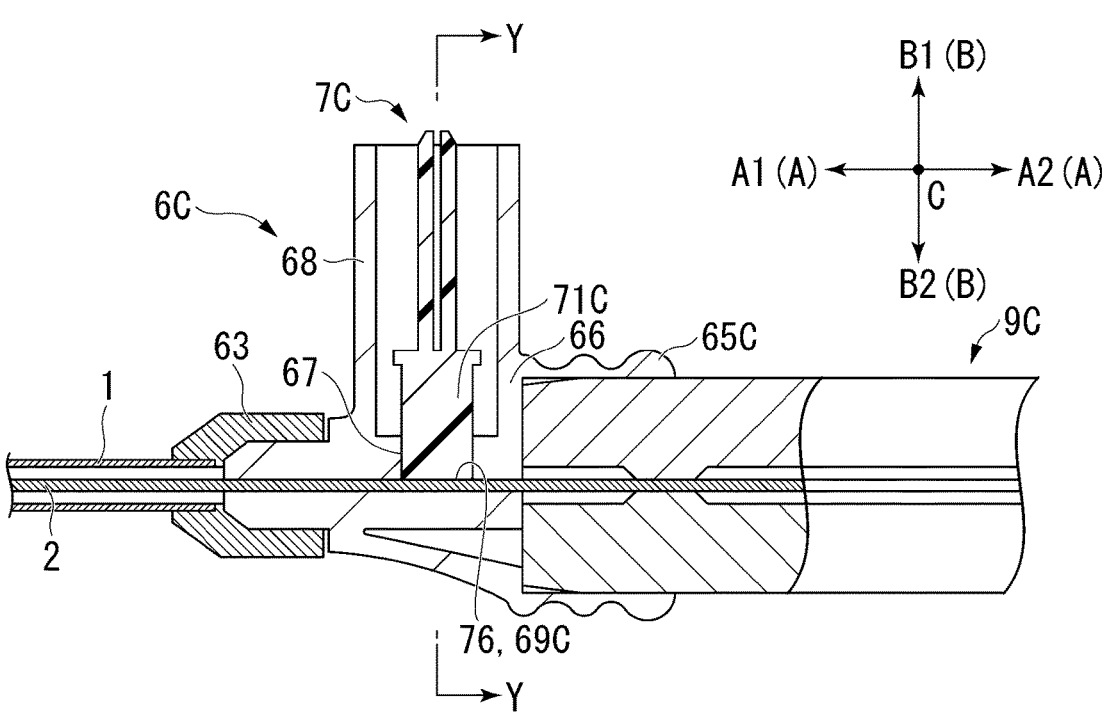
FIG. 20 is a view showing another modification of the conductive member of the handle body.
Figure 21:
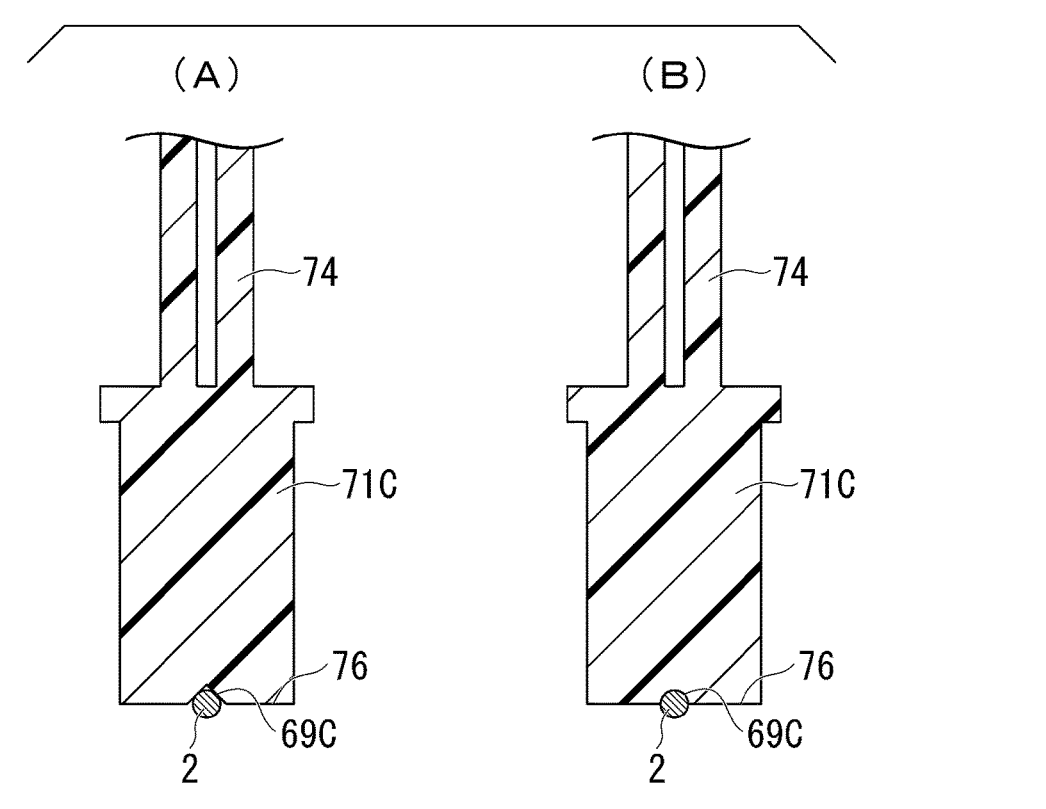
FIG. 21 is a cross-sectional view of the connector along Y-Y of FIG. 20.

In the above embodiment, the conductive member 69 is a columnar member, but the mode of the conductive member is not limited to this. FIG. 20 shows a conductive member 69C that is a modification of the conductive member 69. The conductive member 69C is integrally formed with the connector 7C and is a recess provided at the end 76 of the inner DI of the connector 7C. FIG. 21 is a cross-sectional view of connector 7C along Y-Y in FIG. 20. The conductive member 69C may be a recess having a polygonal cross section perpendicular to the longitudinal axis direction A, as shown in FIG. 21(A). As shown in FIG. 21(B), the conductive member 69C may be an arcuate recess whose cross section perpendicular to the longitudinal axis direction A follows the outer peripheral surface of the operation wire 2.

(Modification)

Figure 22:
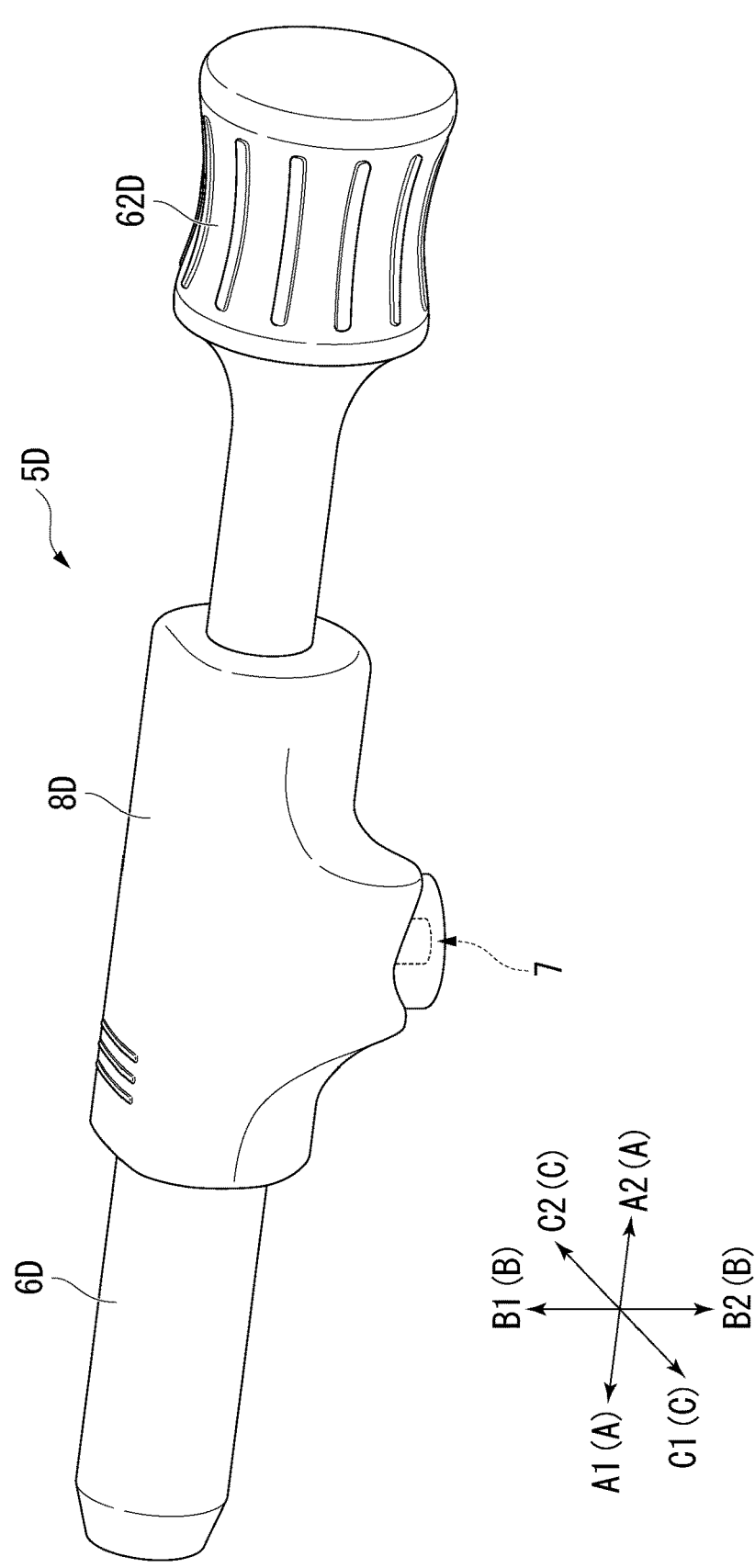
FIG. 22 is a diagram showing a modification of the operation portion of the endoscopic treatment tool according to the first embodiment.
Figure 23:
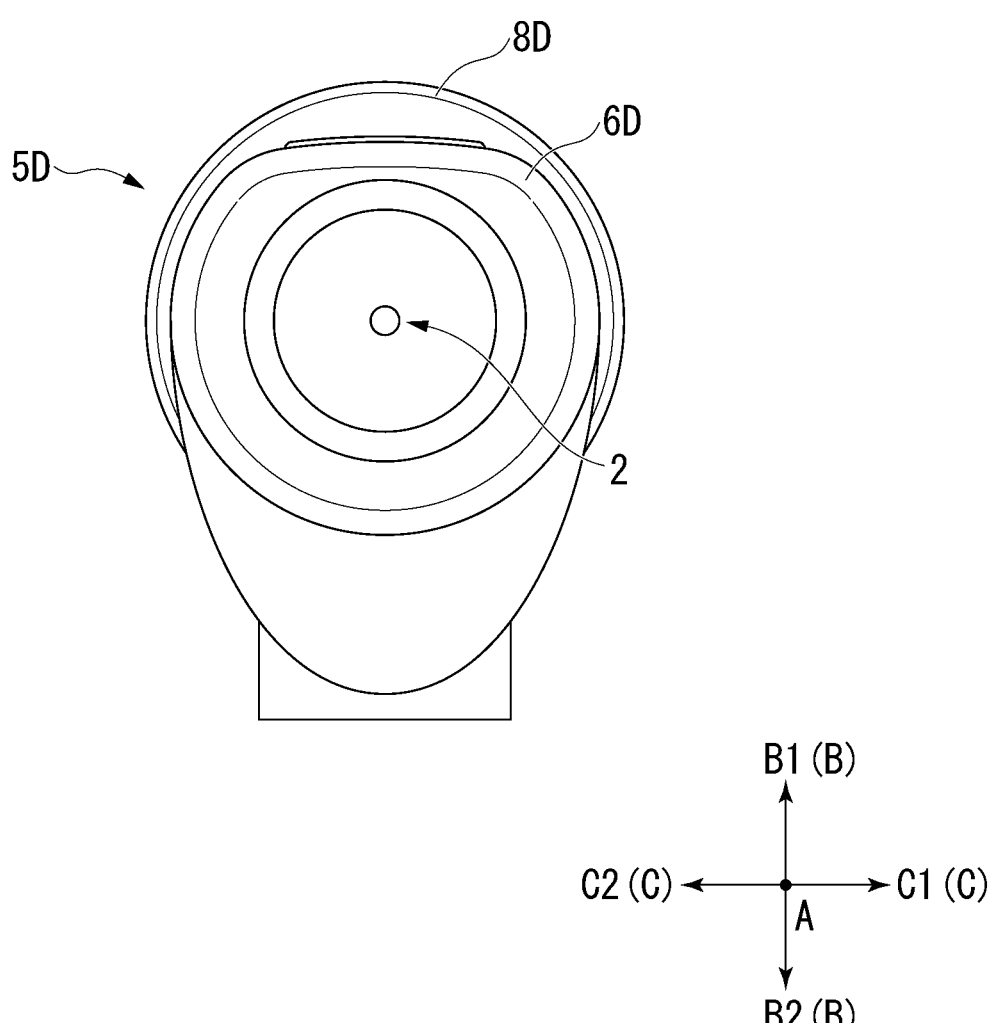
FIG. 23 is a front view of the modification.
Figure 24:
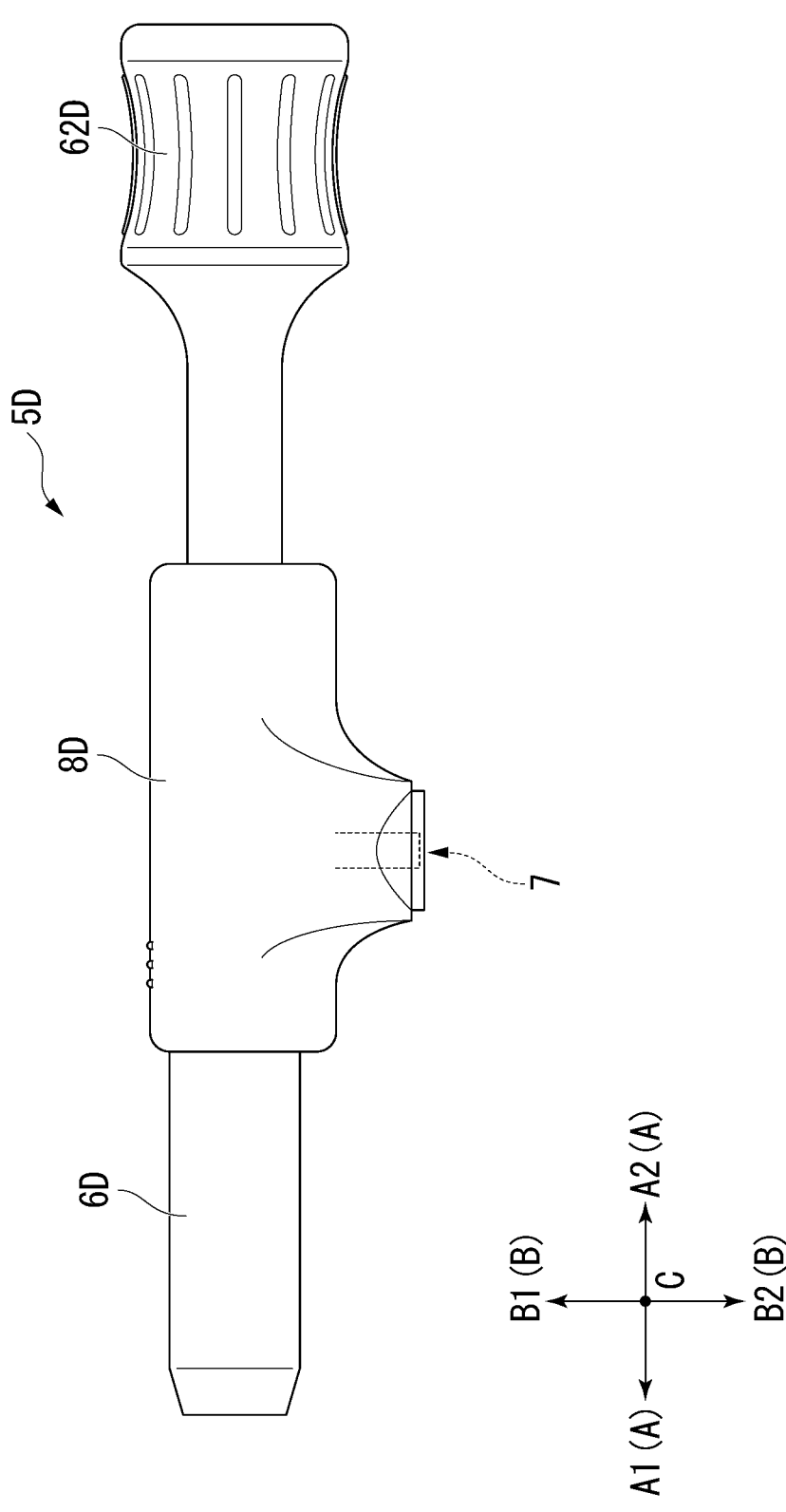
FIG. 24 is a right side view of the modification.
Figure 25:
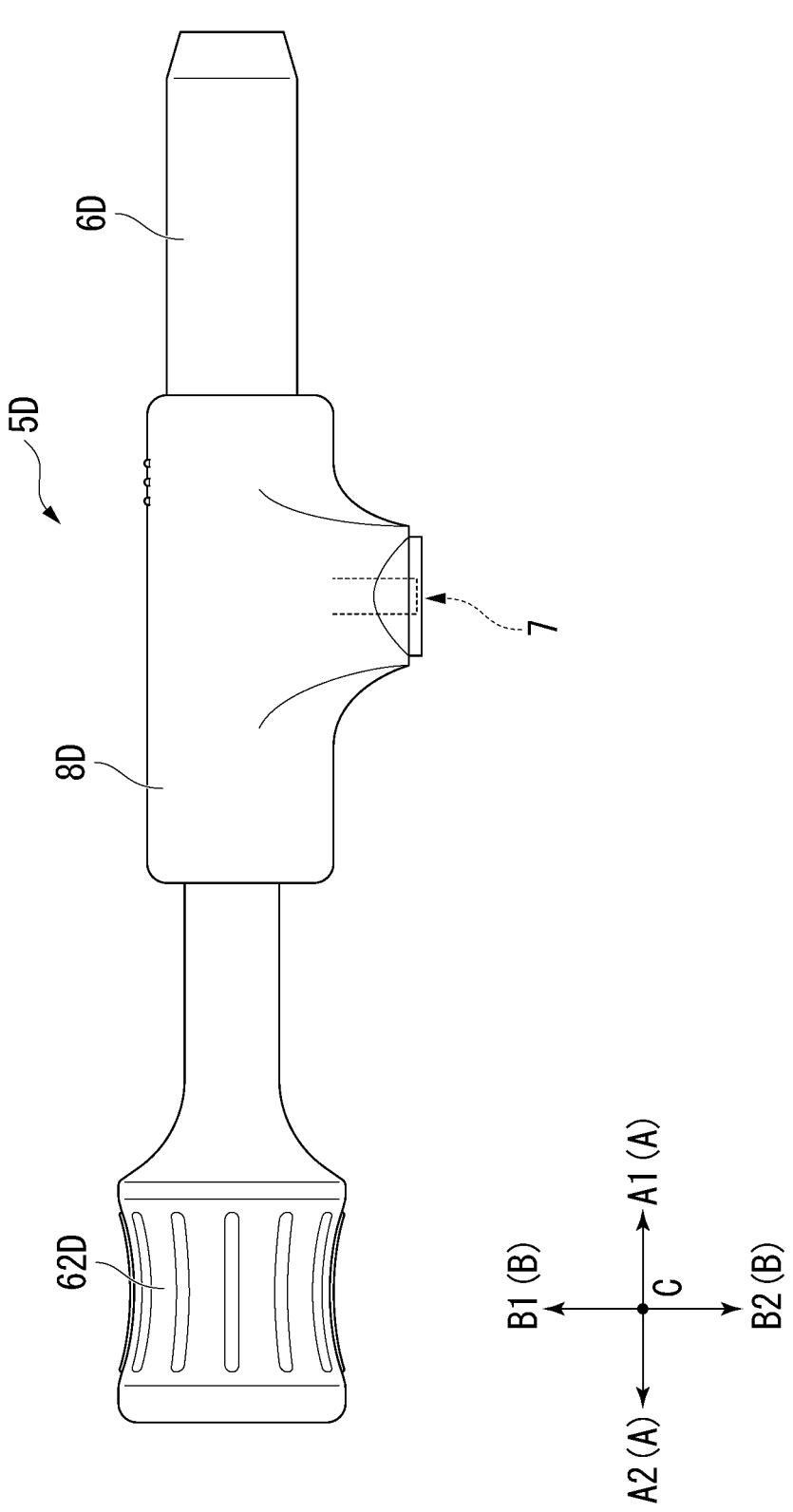
FIG. 25 is a left side view of the modified example.
Figure 26:
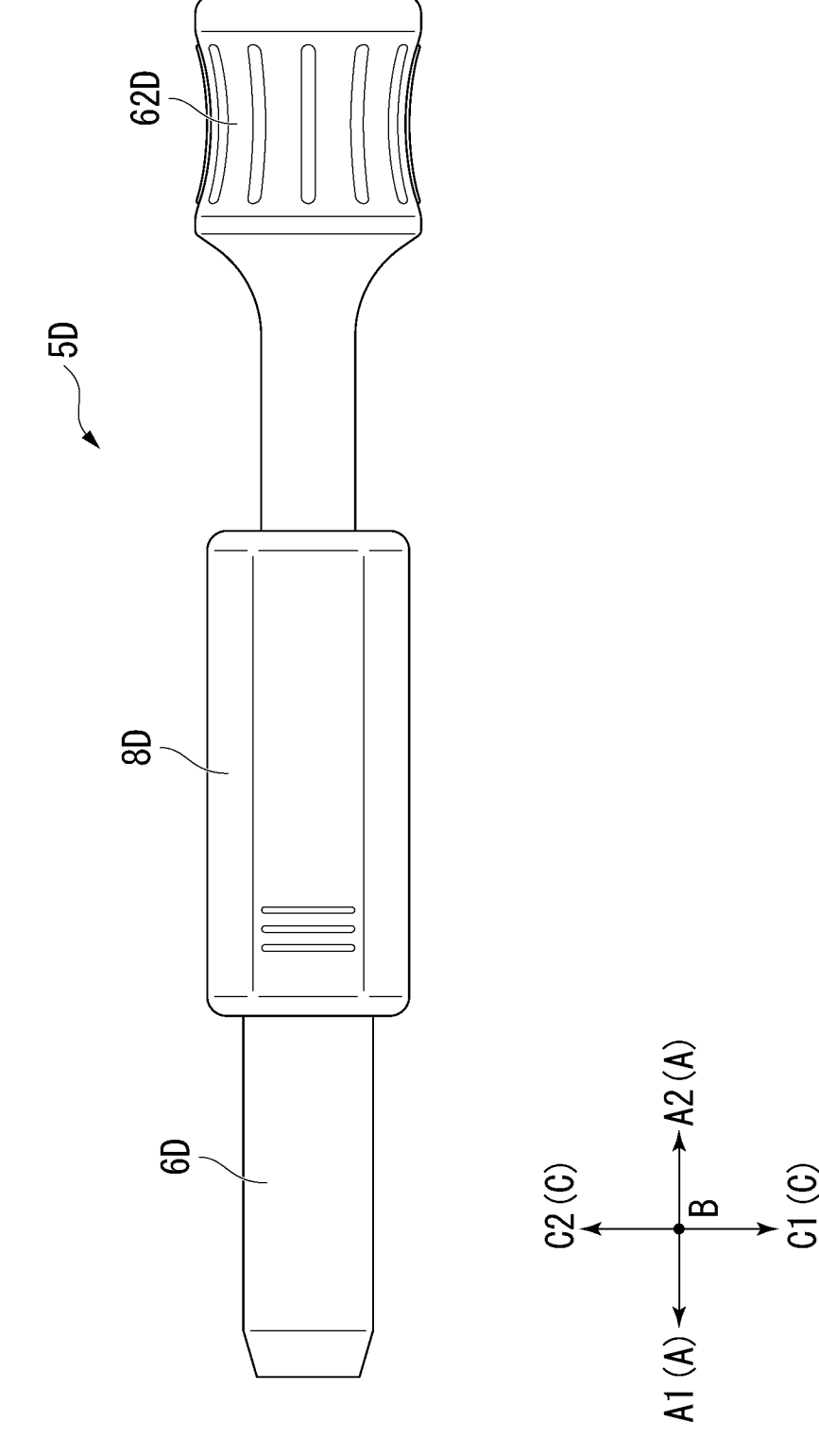
FIG. 26 is a plan view of the modification.
Figure 27:
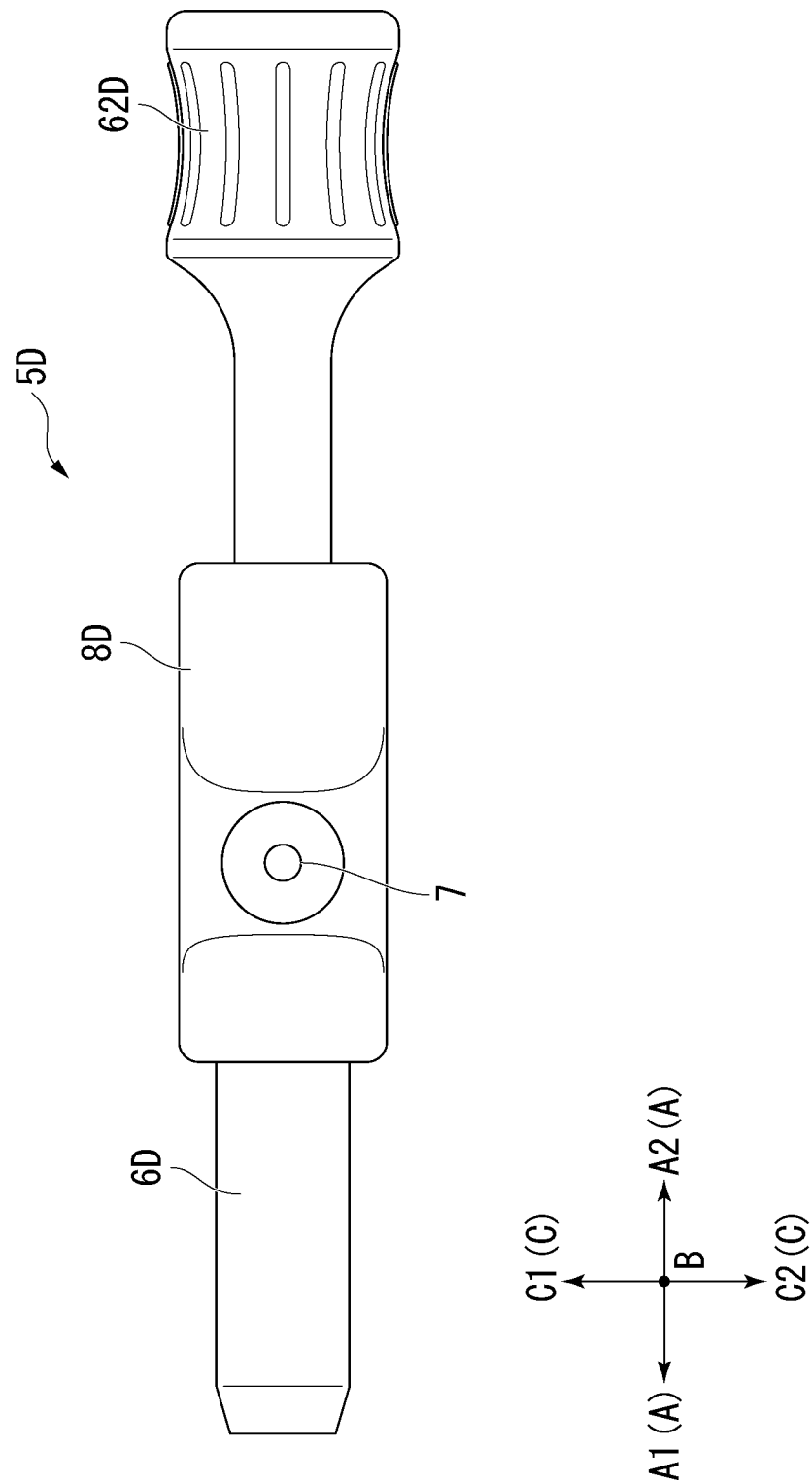
FIG. 27 is a bottom view of the modification.
Figure 28:
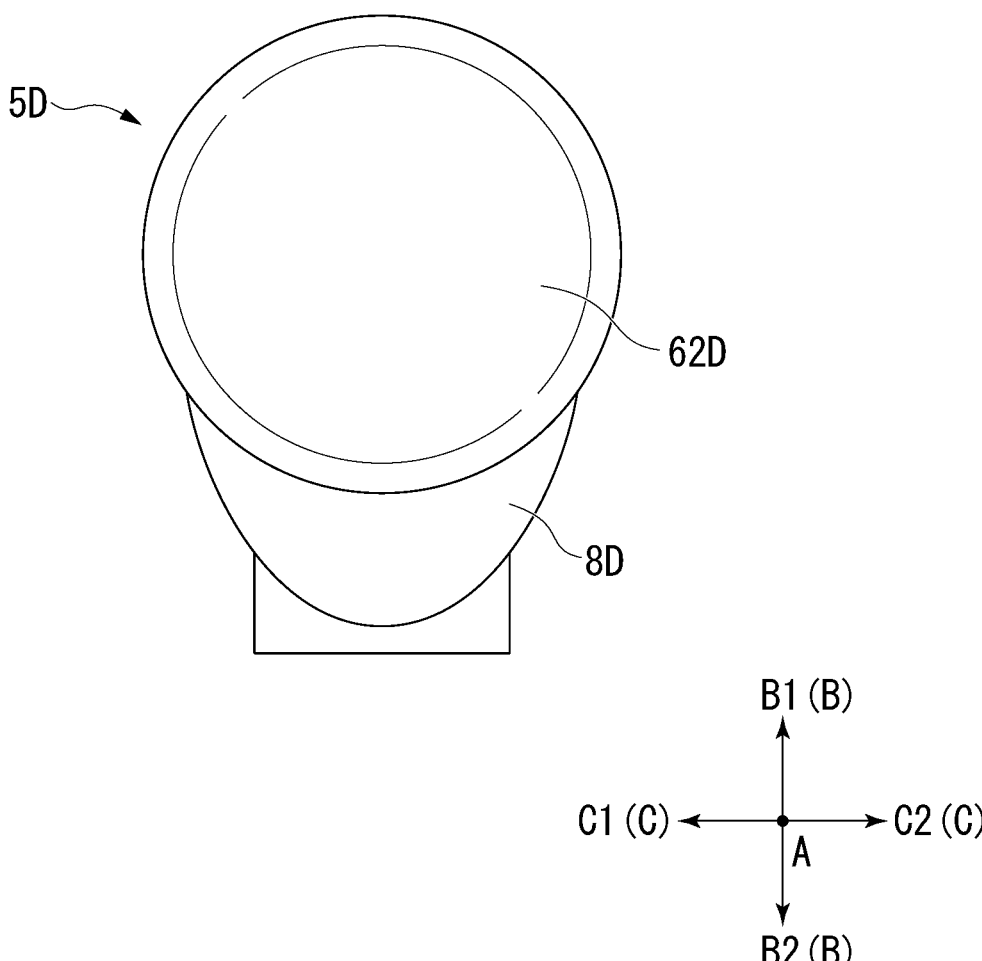
FIG. 28 is a rear view of the modified example.

FIG. 22 is a diagram showing an operation portion 5D which is a modification of the operation portion 5 of the endoscopic treatment tool 100 according to the first embodiment. FIG. 23 is a front view of the operation portion 5D. FIG. 24 is a right side view of the operation portion 5D. FIG. 25 is a left side view of the operation portion 5D. FIG. 26 is a plan view of the operation portion 5D. An operation portion 5D is a bottom view of the modified example. FIG. 28 is a rear view of the operation portion 5D.

The operation portion 5D includes a handle body 6D, a connector 7, a slider 8D, and a rotating handle (not shown). In the operation portion 5D, the connector 7 is attached to the slider 8D. The handle body 6D is formed in a substantially cylindrical shape and has a grip 62D at its proximal end. The grip 62D is formed in a columnar shape having a constriction on the outer periphery. The slider 8D is attached to the outer peripheral portion of the handle body 6D so as to be able to advance and retreat in the longitudinal axis direction A.

What is claimed is:

1. An endoscope treatment tool, comprising:
a sheath;
a handle body;
a wire;
a treatment portion connected to a distal end of the wire and arranged on a distal end side of the sheath;
a rotating handle rotatable with respect to the handle body; and
a conductive connector attached to the handle body and having an insertion passage through which the wire is inserted,
wherein the wire is movable relative to the conductive connector in a wire movement direction to advance and retreat in a direction of a longitudinal axis of the sheath,
wherein the wire is rotatable around the longitudinal axis of the sheath,
wherein the conductive connector extends in a direction that intersects the wire movement direction, wherein the rotating handle is fixed to the handle body in the direction of the longitudinal axis of the sheath and is configured to be rotatable around the longitudinal axis of the sheath, and
wherein a proximal end of the wire is connected to the rotating handle.

2. The endoscopic treatment tool according to claim 1, wherein, when the conductive connector is in a first position, a gap is present between a surface of the insertion passage of the conductive connector and an outer surface of the wire,
wherein, when the conductive connector moves from the first position in a first direction, the surface of the insertion passage contacts the wire on a first portion of the outer surface of the wire that is oriented toward a second direction,
wherein the first direction is a radial direction relative to the wire, and
wherein the second direction is opposite to the first direction.

3. The endoscopic treatment tool according to claim 2, wherein, when the conductive connector moves from the first position in the second direction, the surface of the insertion passage contacts the wire on a second portion of the outer surface of the wire that is oriented toward the first direction.

4. The endoscopic treatment tool according to claim 1, wherein the rotating handle is provided on a proximal side of the handle body.

5. The endoscopic treatment tool according to claim 1, wherein a clearance between the conductive connector and the handle body is larger than a gap between the insertion passage and the wire.

6. The endoscopic treatment tool according to claim 1, further comprising:
a slider translatable with respect to the rotating handle to advance and retreat in a direction of a longitudinal axis of the handle body,
wherein the rotating handle is translatable with respect to the handle body to advance and retreat in the direction of the longitudinal axis of the handle body and is rotatable with respect to the longitudinal axis of the handle body, and
wherein a proximal end of the wire is connected to the slider.

7. The endoscopic treatment tool according to claim 6, wherein the rotating handle is provided on a proximal side of the handle body.

8. The endoscopic treatment tool according to claim 6, wherein the handle body has a conductive member that electrically connects the wire and the conductive connector.

9. The endoscopic treatment tool according to claim 8, wherein the conductive member has a columnar shape.

10. The endoscope treatment tool according to claim 1, wherein a slider is positioned on the rotating handle and is movable in a back and forth direction.

11. The endoscope treatment tool according to claim 1, wherein the handle body has a conductive member that electrically connects the wire and the conductive connector, and
wherein the conductive member is a spring.

12. An endoscope treatment tool, comprising:
a sheath;
a handle body;
a wire;
a treatment portion connected to a distal end of the wire and arranged on a distal end side of the sheath;

a rotating handle rotatable with respect to the handle body;

a slider configured to advance and retreat in a direction of a longitudinal axis of the handle body; and a conductive connector attached to the slider and having an insertion passage through which the wire is inserted, wherein the wire is movable relative to the conductive connector in a wire movement direction to advance and retreat in a direction of a longitudinal axis of the sheath, wherein the wire is rotatable around the longitudinal axis of the sheath, wherein the conductive connector extends in a direction that intersects the wire movement direction, wherein the rotating handle is configured to be rotatable around the longitudinal axis of the sheath, and wherein a proximal end of the wire is connected to the slider.

13. The endoscopic treatment tool according to claim 12, wherein, when the conductive connector is in a first position, a gap is present between a surface of the insertion passage of the conductive connector and an outer surface of the wire, wherein, when the conductive connector moves from the first position in a first direction, the surface of the insertion passage contacts the wire on a first portion of the outer surface of the wire that is oriented toward a second direction, wherein the first direction is a radial direction relative to the wire, and wherein the second direction is opposite to the first direction.

14. The endoscopic treatment tool according to claim 13, wherein, when the conductive connector moves from the first position in the second direction, the surface of the insertion passage contacts the wire on a second portion of the outer surface of the wire that is oriented toward the first direction.

15. The endoscopic treatment tool according to claim 12, wherein the rotating handle is provided on a distal end side of the slider.

16. The endoscopic treatment tool according to claim 15, further comprising:

a pipe translatable with respect to the rotating handle to advance and retreat along the longitudinal axis of the handle body and rotatable with respect to the longitudinal axis around the longitudinal axis of the handle body, wherein a proximal end of the pipe is attached to the proximal end of the wire, and wherein, with respect to the slider, the pipe is rotatable about the longitudinal axis of the handle body and is non-translatable in the direction of the longitudinal axis of the handle body.

17. The endoscopic treatment tool according to claim 12, wherein a clearance between the conductive connector and the slider is larger than a gap between the insertion passage and the wire.

18. An endoscope treatment tool, comprising:

a sheath;

a handle body;

a wire;

a treatment portion connected to a distal end of the wire and arranged on a distal end side of the sheath;

a rotating handle rotatable with respect to the handle body; and a conductive connector attached to the handle body and having an insertion passage through which the wire is inserted, wherein the wire is movable relative to the conductive connector in a wire movement direction to advance and retreat in a direction of a longitudinal axis of the sheath, wherein the wire is rotatable around the longitudinal axis of the sheath, wherein the conductive connector extends in a direction that intersects the wire movement direction, wherein the rotating handle is translatable with respect to the handle body to advance and retreat in the direction of the longitudinal axis of the handle body and is rotatable around the longitudinal axis of the handle body, wherein a proximal end of the wire is connected to the rotating handle, and wherein the rotating handle is provided on a proximal side of the handle body.

19. The endoscopic treatment tool according to claim 18, wherein, when the conductive connector is in a first position, a gap is present between a surface of the insertion passage of the conductive connector and an outer surface of the wire, wherein, when the conductive connector moves from the first position in a first direction, the surface of the insertion passage contacts the wire on a first portion of the outer surface of the wire that is oriented toward a second direction, wherein the first direction is a radial direction relative to the wire, and wherein the second direction is opposite to the first direction.

20. The endoscopic treatment tool according to claim 19, wherein, when the conductive connector moves from the first position in the second direction, the surface of the insertion passage contacts the wire on a second portion of the outer surface of the wire that is oriented toward the first direction.

* * * * *